United States Patent
Koshio et al.

(10) Patent No.: US 7,169,772 B2
(45) Date of Patent: Jan. 30, 2007

(54) 4,4-DIFLUORO-1,2,3,4-TETRAHYDRO-5H-1-BENZAZEPINE DERIVATIVES OR SALTS THEREOF

(75) Inventors: Hiroyuki Koshio, Tsukuba (JP); Issei Tsukamoto, Tsukuba (JP); Takahiro Kuramochi, Tsukuba (JP); Seijiro Akamatsu, Tsukuba (JP); Chikashi Saitoh, Tsukuba (JP)

(73) Assignee: Astellas Pharma Inc., Tokyo (JP)

( * ) Notice: Subject to any disclaimer, the term of this patent is extended or adjusted under 35 U.S.C. 154(b) by 257 days.

(21) Appl. No.: 10/495,494

(22) PCT Filed: Nov. 13, 2002

(86) PCT No.: PCT/JP02/11842

§ 371 (c)(1),
(2), (4) Date: May 13, 2004

(87) PCT Pub. No.: WO03/042181

PCT Pub. Date: May 22, 2003

(65) Prior Publication Data

US 2005/0004103 A1    Jan. 6, 2005

(30) Foreign Application Priority Data

Nov. 16, 2001 (JP) ............................. 2001-350909
Aug. 30, 2002 (JP) ............................. 2002-252931

(51) Int. Cl.
*A61P 7/12* (2006.01)
*A61K 31/55* (2006.01)
*C07D 223/16* (2006.01)

(52) U.S. Cl. .................... 514/213.01; 540/593
(58) Field of Classification Search .......... 514/213.01; 540/593
See application file for complete search history.

(56) References Cited

U.S. PATENT DOCUMENTS

| | | | |
|---|---|---|---|
| 5,710,150 A | 1/1998 | Taniguchi et al. | 514/213 |
| 5,753,644 A | 5/1998 | Ogawa et al. | 514/213 |
| 6,096,736 A | 8/2000 | Ogawa et al. | 514/213 |
| 6,340,678 B1 | 1/2002 | Matsuhisa et al. | 514/213.01 |

FOREIGN PATENT DOCUMENTS

JP    09-221475    8/1997

OTHER PUBLICATIONS

Kondo et al., Novel Design of Nonpeptide AVP V2 Receptor Agonists: Structural Requirements for an Agonist Having 1-(4-Aminobenzoyl)-2,3,4,5-tetrahydro-1H-1-benzazepine as a Template, J. of Medicinal Chemistry, Nov. 2000, vol. 43, No. 23, pp. 4388-4397.*

* cited by examiner

*Primary Examiner*—Brenda Coleman
(74) *Attorney, Agent, or Firm*—Finnegan, Henderson, Farabow, Garrett & Dunner LLP

(57) ABSTRACT

4,4-difluoro-1,2,3,4-tetrahydro-5H-1-benzazepine derivatives, which have excellent arginine vasopressin $V_2$ activity and are useful for a drug for the treatment of central diabetes insipidus and/or nocturia.

8 Claims, No Drawings

4,4-DIFLUORO-1,2,3,4-TETRAHYDRO-5H-1-BENZAZEPINE DERIVATIVES OR SALTS THEREOF

This application is the National Stage of International Application No. PCT/JP02/11842, filed Nov. 13, 2002.

1. Technical Field of the Invention

The present invention relates to a novel 4,4-difluoro-1,2,3,4-tetrahydro-5H-1-benzazepine derivative or a salt thereof, which is useful as a medicament, especially as a drug for the treatment of central diabetes insipidus or nocturia, and to a medicament comprising the compound as an active ingredient.

2. Background Art

Arginine vasopressin (AVP) is a peptide consisting of 9 amino acids, which is biosynthesized and secreted from the hypothalamus/pituitary gland. AVP receptors are classified into three subtypes, i.e. $V_{1a}$, $V_{1b}$, and $V_2$. It is known that the main pharmaceutical effects of AVP in peripheral are vasoconstriction through the $V_{1a}$ receptor, and antidiuresis through the $V_2$ receptor. As a medicament for selectively stimulating $V_2$ receptors, desmopressin has been synthesized (by deleting the amino acid of cystein in position 1 of AVP, and converting arginine of position 8 into a d form) and is used in the treatment of central diabetes insipidus (Journal of Japanese Academy of Endocrinology, 54, 676–691, 1978). However, an oral agent of desmopressin has very low biological availability and requires a high dose. Thus, desmopressin formulation is expensive, and side effect based on variation of absorption according to individuals is often recognized. Therefore, there is a demand for the development of a nonpeptide antidiuretic agent, which selectively stimulates $V_2$ receptors and has high biological availability.

In addition, according to diversified medical treatment and aging population, it has become rare to employ a single medicine, and in most cases, plural kinds of medicines are administrated simultaneously or at intervals. The same applies to the field of medicament for stimulating AVP. A medicine is inactivated by the action of a medicine metabolism enzyme in the liver and is converted into a metabolite, and among these enzymes, cytochrome P450 (CYP) is most important. Several types of molecular species of CYP exist, but if plural kinds of medicines that are metabolized by the same molecular species of CYP compete on the metabolism enzyme, it is believed that metabolism is somewhat inhibited, although the extent of the inhibition varies depending on affinity of each of the medicines for CYP. As a result, interactions between medicines such as blood concentration increase or blood half life prolongation, etc. are expressed.

Such interactions between medicines are not desirable, except in a case where synergism is intended, and often result in unexpected side effect. Therefore, there is a demand for the development of pharmaceuticals that have low affinity for CYP and between which causes little concern about interactions between other medicines.

As conventional nonpeptide compounds that selectively stimulate $V_2$ receptor and show antidiuretic effects, tricyclic compounds represented by the general Formula (A), general Formula (B), or general Formula (C) are disclosed in WO 99/06409, WO 99/06403, and WO 00/46224.

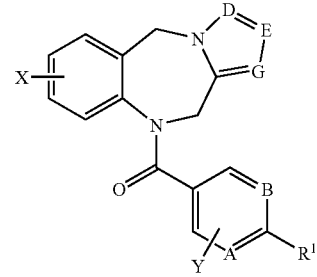

(A)

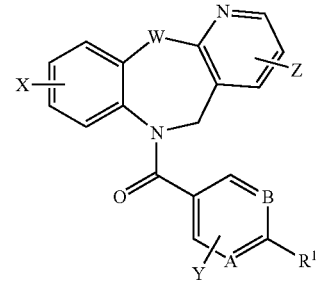

(B)

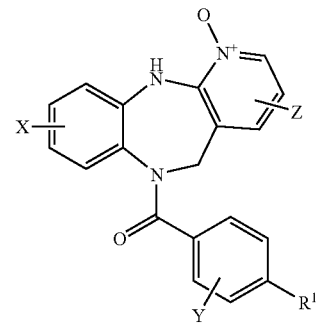

(C)

(Each symbol is as defined in the above publications.)

Additionally, condensed azepine derivatives represented by the general Formula (D) are disclosed in WO 01/49682.

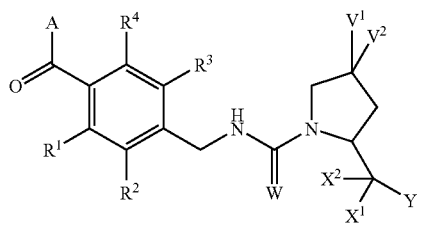

(D)

(Each symbol is as defined in the above publication.)

Also, benzazepine derivatives represented by the general Formula (E) are disclosed in WO 97/22591 and Japanese Patent No. 2926335, and benzoheterocyclic compounds represented by the general Formula (F) or general Formula (G) are disclosed in Japanese Patent No. 3215910, and Japanese Patent Publication Nos. tokkaihei 11-349570 and tokkai 2000-351768.

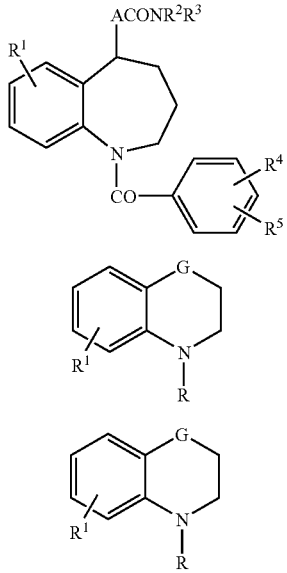

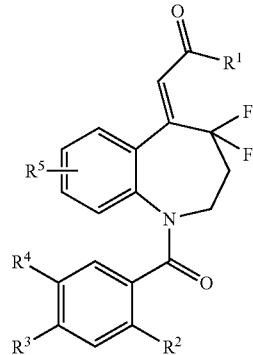

(Each symbol is as defined in the above publications.)

However, none of the publications discloses 4,4-difluoro-1,2,3,4-tetrahydro-5H-1-benzazepine derivatives.

In addition, although WO 95/06035 and WO 98/39325, and Japanese Patent Publication No. tokkaihei 9-221475 disclose 4,4-difluoro-1,2,3,4-tetrahydro-5H-1-benzazepine derivatives that have AVP receptor antagonist effects or oxytocin receptor antagonist effects, none of them discloses $V_2$ receptor agonist effects and efficacy in treating central diabetes insipidus and nocturia.

Accordingly, there is a demand for the development of a nonpeptide antidiuretic agent that is useful in the treatment of central diabetes insipidus and/or nocturia, and has high biological availability.

DISCLOSURE OF THE INVENTION

The inventors, as a result of assiduous studies on compounds having $V_2$ receptor agonist effects and efficacy in treating central diabetes insipidus and/or nocturia, discovered that 4,4-difluoro-1,2,3,4-tetrahydro-5H-1-benzazepin derivatives have such effects, and completed the present invention. Additionally, the inventors discovered that the compound of the present invention has a very low inhibitory activity against medicine metabolism enzymes of CYP3A4 and CYP2C9, compared with known benzazepine derivatives having $V_2$ receptor agonist activity, and completed the present invention.

The object of the present invention is, to provide a novel 4,4-difluoro-1,2,3,4-tetrahydro-5H-1-benzazepine derivative represented by the following general Formula (I) or a pharmaceutically acceptable salt thereof, which are useful for a drug for the treatment of central diabetes insipidus and/or nocturia; and a drug comprising the compound as an active ingredient, particularly a drug for the treatment of central diabetes insipidus or nocturia, or a drug as arginine vasopressin $V_2$ receptor agonist.

wherein each symbol has the following meaning:

$R^1$: —OH, —O-lower alkyl, or an optionally substituted amino;

$R^2$: a lower alkyl which may be substituted with one or more halogen, or a halogen;

$R^3$, $R^4$: one is —H, a lower alkyl, or a halogen, and the other is an optionally substituted nonaromatic cyclic amino, or an optionally substituted aromatic cyclic amino; and $R^5$: —H, a lower alkyl, or a halogen.

The compound of the present invention is characterized by having two fluoro groups on a carbon atom in a benzazepine ring, which carbon atom is adjacent to a carbon atom substituted by substituted methylidene group in the ring. Further, since the double bond conjugated with a carbonyl group is not isomerized due to the two fluoro groups, the compound of the invention has a sufficient stability even in a living body.

Preferred is a novel 4,4-difluoro-1,2,3,4-tetrahydro-5H-1-benzazepine derivative represented by the general Formula (I) or a pharmaceutically acceptable salt thereof, wherein $R^1$ is a group represented by the general Formula (II), or a group represented by the general Formula (III).

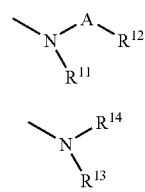

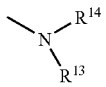

wherein each symbol has the following meaning:

A: a single bond, lower alkylene, or -lower alkylene-C(=O)—;

$R^{11}$: a lower alkyl which may be substituted with a group selected from the group consisting of —OH, —O-lower alkyl, —CO$_2$H, —CO$_2$-lower alkyl, and carbamoyl which may be substituted with one or two lower alkyl, or —H;

$R^{12}$: (1) when A is a single bond or lower alkylene, $R^{12}$ is aryl, cycloalkyl, aromatic heterocycle, or nonaromatic heterocycle, each of which may be substituted, or —H, —OH, —O-lower alkyl, —CO$_2$H, —CO$_2$-lower alkyl, or carbamoyl which may be substituted with one or two lower alkyl.

(2) when A is -lower alkylene-C(=O)—, $R^{12}$ is a group represented by the general Formula (III), or a group represented by the general Formula (IV);

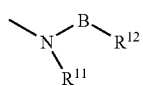
(IV)

B: a single bond or lower alkylene;

R$^{13}$, R$^{14}$: optionally substituted nonaromatic cyclic amino group bonded together with an adjacent nitrogen atom.

More preferred is a novel 4,4-difluoro-1,2,3,4-tetrahydro-5H-1-benzazepine derivative represented by the general Formula (I) or a pharmaceutically acceptable salt thereof, wherein R$^1$ is a group represented by the general Formula (II), or a group represented by the general Formula (III); R$^3$ is an optionally substituted nonaromatic cyclic amino group, or an optionally substituted aromatic cyclic amino group; R$^4$ is —H, a lower alkyl, or a halogen; and R$^5$ is —H.

Still more preferred is a novel 4,4-difluoro-1,2,3,4-tetrahydro-5H-1-benzazepine derivative represented by the general Formula (I) or a pharmaceutically acceptable salt thereof, wherein R$^1$ is a group represented by the general Formula (II), or a group represented by the general Formula (III); R$^3$ is an optionally substituted nonaromatic cyclic amino, or an optionally substituted aromatic cyclic amino; R$^4$ is —H; and R$^5$ is —H.

Most preferred is a novel 4,4-difluoro-1,2,3,4-tetrahydro-5H-1-benzazepine derivative represented by the general Formula (I) or a pharmaceutically acceptable salt thereof, wherein R$^1$ is a group represented by the general Formula (II), or a group represented by the general Formula (III); R$^3$ is methylpyrazolyl, pyrrolidinyl, or methylpyrrolidinyl; R$^4$ is —H; and R$^5$ is —H.

Among these compounds, a compound or a pharmaceutically acceptable salt thereof selected from the compound group A and the compound group B are particularly preferable, and a compound or a pharmaceutically salt thereof selected from the compound group A are more preferable.

The compound group A includes:

(2Z)-2-{1-[2-chloro-4-(3-methyl-1H-pyrazoly-yl)benzoyl]-4,4-difluoro-1,2,3,4-tetrahydro-5H-1-benzazepin-5-ylidene}-N-(pyridin-2-ylmethyl)acetamide;

(2Z)-N-(2-amino-2-oxoethyl)-2-[1-(2-chloro-4-pyrrolidin-1-ylbenzoyl)-4,4-difluoro-1,2,3,4-tetrahydro-5H-1-benzazepin-5-ylidene]acetamide;

(2Z)-2-{4,4-difluoro-1-[4-(3-methyl-1H-pyrazol-1-yl)-2-(trifluoromethyl)benzoyl]1-1,2,3,4-tetrahydro-5H-1-benzazepin-5-ylidene}acetamide;

(2Z)-N-(2-amino-2-oxoethyl)-2-{4,4-difluoro-1-[4-(3R)-3-methylpyrrolidin-1-yl]-2-(trifluoromethyl)benzoyl]-1,2,3,4-tetrahydro-5H-1-benzazepin-5-ylidene}acetamide;

(2Z)-2-{4,4-difluoro-1-[4-[(3R)-3-methylpyrrolidin-1yl]-2-(trifluoromethyl)benzoyl]-1,2,3,4-tetrahydro-5H-1-benzazepin-5-ylidene}-N-(2-hydroxyethyl)acetamide;

(2Z)-N-(2-amino-2-oxoethyl)-2-{4,4-difluoro-1-[4-(3S)-3-methylpyrrolidin-1-yl]-2-(trifluoromethyl)benzoyl]-1,2,3,4-tetrahydro-5H-1-benzazepin-5-ylidene}acetamide;

(2Z)-2-{4,4-difluoro-1-[4-[(3-methyl-1H-pyrazol-1-yl)-2-(trifluoromethyl)benzoyl]-1,2,3,4-tetrahydro-5H-1-benzazepin-5-ylidene]-N-(2-hydroxyethyl)acetamide;

(2Z)-N-(2-amino-2-oxoethyl)-2-(1-{2-chloro-4-[(3R)-3-methylpyrrolidin-1-yl]benzoyl}-4,4-difluoro-1,2,3,4-tetrahydro-5H-1-benzazepin-5-ylidene)acetamide;

(2Z)-N-(2-amino-2-oxoethyl)-2-(1-{2-chloro-4-[(3S)-3-methylpyrrolidin-1-yl]benzoyl}-4,4-difluoro-1,2,3,4-tetrahydro-5H-1-benzazepin-5-ylidene)acetamide;

(2Z)-2-{4,4-difluoro-1-[4-(4-methyl-1H-pyrazol-1-yl)-2-(trifluoromethyl)benzoyl]-1,2,3,4-tetrahydro-5H-1-benzazepin-5-ylidene}acetamide;

(2Z)-N-(2-amino-2-oxoethyl)-2-{1-[4-(3,4-dimethylpyrrolidin-1-yl)-2-(trifluoromethyl)benzoyl]-4,4-difluoro-1,2,3,4-tetrahydro-5H-1-benzazepin-5-ylidene}acetamide; and (2Z)-2-{4,4-difluoro-1-[2-methyl-4-(3-methyl-1H-pyrazol-1-yl)benzoyl]-1,2,3,4-tetrahydro-5H-1-benzazepin-5-ylidene}acetamide.

The compound group B includes:

(2Z)-2-{1-[2-chloro-4-(3-methyl-1H-pyrazol-1-yl)benzoyl]-4,4-difluoro-1,2,3,4-tetrahydro-5H-1-benzazepin-5-ylidene}-N-[3-(hydroxymethyl)phenyl]acetamide;

(2Z)-2-{1-[2-chloro-4-(3-methyl-1H-pyrazol-1-yl)benzoyl]-4,4-difluoro-1,2,3,4-tetrahydro-5H-1-benzazepin-5-ylidene}-N-[4-(hydroxymethyl)phenyl]acetamide;

(2Z)-2-{1-[2-chloro-4-(3-methyl 1H-pyrazol-1-yl)benzoyl]-4,4-difluoro-1,2,3,4-tetrahydro-5H-1-benzazepin-5-ylidene}-N-[(6-methylpyridin-2-yl)methyl]acetamide;

3-[((2Z)-2-{1-[2-chloro-4-(3-methyl-1H-pyrazol-1-yl)benzoyl]-4,4-difluoro-1,2,3,4-tetrahydro-5H-1-benzazepin-5-ylidene}acetyl)amino]benzamide;

4-[((2Z)-2-{1-[2-chloro-4-(3-methyl-1H-pyrazol-1-yl)benzoyl]-4,4-difluoro-1,2,3,4-tetrahydro-5H-1-benzazepin-5-ylidene}acetyl)amino]benzamide;

4-{[((2Z)-2-{1-[2-chloro-4-(3-methyl-1H-pyrazol-1-yl)benzoyl]-4,4-difluoro-1,2,3,4-tetrahydro-5H-1-benzazepin-5-ylidene}acetyl)amino]methyl}benzamide;

(2Z)-2-{1-[2-chloro-4-(3-methyl-1H-pyrazol-1-yl)benzoyl]-4,4-difluoro-1,2,3,4-tetrahydro-5H-1-benzazepin-5-ylidene}-N-[3-(methoxymethyl)phenyl]acetamide;

(2Z)-2-{1-[2-chloro-4-(3-methyl-1H-pyrazol-1-yl)benzoyl]-4,4-difluoro-1,2,3,4-tetrahydro-5H-1-benzazepin-5-ylidene}-N-[3-(1-hydroxyethyl)phenyl]acetamide;

(2Z)-2-{1-[2-chloro-4-(3-methyl-1H-pyrazol-1-yl)benzoyl]-4,4-difluoro-1,2,3,4-tetrahydro-5H-1-benzazepin-5-ylidene}-N-[3-(methylsulfonyl)phenyl]acetamide;

(2Z)-N-(3-acetylphenyl)-2-{1-[2-chloro-4-(3-methyl-1H-pyrazol-1-yl)benzoyl]-4,4-difluoro-1,2,3,4-tetrahydro-5H-1-benzazepin-5-ylidene}acetamide;

(2Z)-2-{1-[2-chloro-4-(3-methyl-1H-pyrazol-1-yl)benzoyl]-4,4-difluoro-1,2,3,4-tetrahydro-5H-1-benzazepin-5-ylidene}-N-(3-methylphenyl)acetamide;

(2Z)-2-{1-[2-chloro-4-(3-methyl-1H-pyrazol-1-yl)benzoyl]-4,4-difluoro-1,2,3,4-tetrahydro-5H-1-benzazepin-5-ylidene}-N-(3-fluorophenyl)acetamide;

(2Z)-2-{1-[2-chloro-4-(3-methyl-1H-pyrazol-1-yl)benzoyl]-4,4-difluoro-1,2,3,4-tetrahydro-5H-1-benzazepin-5-ylidene}-N-[3-(2-hydroxyethyl)phenyl]acetamide;

(2Z)-2-{1-[2-chloro-4-(3-methyl-1H-pyrazol-1-yl)benzoyl]-4,4-difluoro-1,2,3,4-tetrahydro-5H-1-benzazepin-5-ylidene}-N-(2-hydroxy-1,1-dimethylethyl)acetamide;

1-((2Z)-2-{1-[2-chloro-4-(3-methyl-1H-pyrazol-1-yl)benzoyl]-4,4-difluoro-1,2,3,4-tetrahydro-5H-1-benzazepin-5-ylidene}acetyl)piperidine-3-carboxamide;

(2Z)-N-[4-(aminosulfonyl)benzyl]-2-{1-[2-chloro-4-(3-methyl-1H-pyrazol-1-yl)benzoyl]-4,4-difluoro-1,2,3,4-tetrahydro-5H-1-benzazepin-5-ylidene}acetamide;

(2Z)-2-{1-[2-chloro-4-(3-methyl-1H-pyrazol-1-yl)benzoyl]-4,4-difluoro-1,2,3,4-tetrahydro-5H-1-benzazepin-5-ylidene}-N-(2-hydroxycyclohexyl)acetamide;

(2Z)-N-[3-(2-amino-2-oxoethyl)phenyl]-2-{1-[2-chloro-4-(3-methyl-1H-pyrazol-1-yl)benzoyl]-4,4-difluoro-1,2,3,4-tetrahydro-5H-1-benzazepin-5-yliende}acetamide;

3-{3-[((2Z)-2-{1-[2-chloro-4-(3-methyl-1H-pyrazol-1-yl)benzoyl]-4,4-difluoro-1,2,3,4-tetrahydro-5H-1-benzazepin-5-yliende}acetyl)amino]phenyl}propanamide;

(2E)-3-{3-[((2Z)-2-{1-[2-chloro-4-(3-methyl-1H-pyrazol-1-yl)benzoyl]-4,4-difluoro-1,2,3,4-tetrahydro-5H-1-benzazepin-5-yliende}acetyl)amino]phenyl}acrylamide;

(2Z)-2-{1-[2-chloro-4-(3-methyl-1H-pyrazol-1-yl)benzoyl]-4,4-difluoro-1,2,3,4-tetrahydro-5H-1-benzazepin-5-yliende}-N-(2-oxopyrrolidin-3-yl)acetamide;

(2Z)-2-{1-[2-chloro-4-(3-methyl-1H-pyrazol-1-yl)benzoyl]-4,4-difluoro-1,2,3,4-tetrahydro-5H-1-benzazepin-5-yliende}-N-(2-oxotetrahydrofuran-3-yl)acetamide;

3-[((2Z)-2-{1-[2-chloro-4-(3-methyl-1H-pyrazol-1-yl)benzoyl]-4,4-difluoro-1,2,3,4-tetrahydro-5H-1-benzazepin-5-yliende}acetyl)amino]-N-methylbenzamide;

(2Z)-2-{1-[2-chloro-4-(3-methyl-1H-pyrazol-1-yl)benzoyl]-4,4-difluoro-1,2,3,4-tetrahydro-5H-1-benzazepin-5-yliende}-N-{2-[2-(hydroxymethyl)piperidin-1-yl]-2-oxoethyl}acetamide;

(2Z)-2-{1-[2-chloro-4-(3-methyl-1H-pyrazol-1-yl)benzoyl]-4,4-difluoro-1,2,3,4-tetrahydro-5H-1-benzazepin-5-yliende}-N-{2-[3-(hydroxymethyl)piperidin-1-yl]-2-oxoethyl}acetamide;

(2Z)-N-[3-(acetylamino)phenyl]-2-{1-[2-chloro-4-(3-methyl-1H-pyrazol-1-yl)benzoyl]-4,4-difluoro-1,2,3,4-tetrahydro-5H-1-benzazepin-5-yliende}acetamide;

(2Z)-2-{1-[2-chloro-4-(3-methyl-1H-pyrazol-1-yl)benzoyl]-4,4-difluoro-1,2,3,4-tetrahydro-5H-1-benzazepin-5-yliende}-N-(2-oxotetrahydrothiophen-3-yl)acetamide;

(2Z)-2-{1-[2-chloro-4-(3,3-dimethylpyrrolidin-1-yl)benzoyl]-4,4-difluoro-1,2,3,4-tetrahydro-5H-1-benzazepin-5-yliende}-N-(pyridine-2-ylmethyl)acetamide;

(2Z)-2-{1-[2-chloro-4-(3,3-dimethylpyrrolidin-1-yl)benzoyl]-4,4-difluoro-1,2,3,4-tetrahydro-5H-1-benzazepin-5-yliende}acetamide;

(2Z)-N-(2-amino-2-oxoethyl)-2-{1-[2-chloro-4-(3-ethyl-3-methylpyrrolidin-1-yl)benzoyl]-4,4-difluoro-1,2,3,4-tetrahydro-5H-1-benzazepin-5-yliende}acetamide;

(2Z)-N-(2-amino-2-oxoethylyl)-2-{1-[2-chloro-4-(3,3-dimethylpyrrolidin-1-yl)benzoyl]-4,4-difluoro-1,2,3,4-tetrahydro-5H-1-benzazepin-5-yliende}acetamide;

(2Z)-N-(2-amino-2-oxoethylyl)-2-{1-[2-chloro-4-(3-phenylpyrrolidin-1-yl)benzoyl]-4,4-difluoro-1,2,3,4-tetrahydro-5H-1-benzazepin-5-yliende}acetamide;

(2Z)-2-{1-[2-chloro-4-(3,3-dimethylpyrrolidin-1-yl)benzoyl]-4,4-difluoro-1,2,3,4-tetrahydro-5H-1-benzazepin-5-yliende}-N-(2-hydroxyethyl)acetamide;

(2Z)-2-{1-[2-chloro-4-(3-phenylpyrrolidin-1-yl)benzoyl]-4,4-difluoro-1,2,3,4-tetrahydro-5H-1-benzazepin-5-yliende}acetamide;

(2Z)-2-{1-[2-chloro-4-(3-ethyl-3-methylpyrrolidin-1-yl)benzoyl]-4,4-difluoro-1,2,3,4-tetrahydro-5H-1-benzazepin-5-yliende}acetamide;

(2Z)-2-{4,4-difluoro-1-[4-[(3R)-3-methylpyrrolidin-1-yl]-2-(trifluoromethyl)benzoyl]-1,2,3,4-tetrahydro-5H-1-benzazepin-5-yliende}-N-(2-hydroxyethyl)acetamide;

(2Z)-2-{4,4-difluoro-1-[4-[(3R)-3-methylpyrrolidin-1-yl]-2-(trifluoromethyl)benzoyl]-1,2,3,4-tetrahydro-5H-1-benzazepin-5-yliende}acetamide;

(2Z)-2-{1-[2-chloro-5-fluoro-4-(3-methyl-1H-pyrazol-1-yl)benzoyl]-4,4-difluoro-1,2,3,4-tetrahydro-5H-1-benzazepin-5-yliende}acetamide; and (2Z)-2-{1-[2-chloro-4-(3-methyl-1H-pyrazol-1-yl)benzoyl]-4,4-difluoro-1,2,3,4-tetrahydro-5H-1-benzazepin-5-yliende}-N-[4-(1,2-dihydroxyethyl)phenyl]acetamide.

Another object of the present invention is to provide a novel 4,4-difluoro-1,2,3,4-tetrahydro-5H-1-benzazepine derivative represented by the following general Formula (V) or a pharmaceutically acceptable salt thereof, which is a useful intermediate in the preparation of the 4,4-difluoro-1,2,3,4-tetrahydro-5H-1-benzazepine derivative represented by the above general Formula (I) or a pharmaceutically acceptable salt thereof, which is useful in the treatment of central diabetes insipidus and/or nocturia.

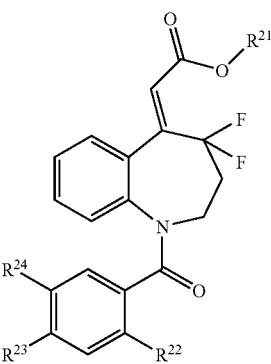

(V)

wherein each symbol has the following meaning, $R^{21}$: lower alkyl, $R^{22}$: chloro or trifluoromethyl, $R^{23}$, $R^{24}$: one is —H, and the other is an optionally protected hydrazino group, and $R^{21}$ is preferably methyl or ethyl, more preferably methyl.

The present invention will be explained in detail herein below.

In the definition of the general formula for the compound of the present invention, the term "lower alkyl" means a monovalent group of a straight or branched carbon chain having 1 to 6 carbon atoms, and its examples include methyl, ethyl, propyl, butyl, pentyl, and hexyl, and structural isomers thereof such as isopropyl, tert-butyl, and the like, of which alkyl having 1 to 3 carbon atoms such as methyl, ethyl, propyl, and isopropyl are preferred.

The term "lower alkenyl" means a monovalent group of a straight or branched unsaturated carbon chain having 2 to 6 carbon atoms, and its examples include vinyl, allyl, 1-butenyl, 2-butenyl, 1-hexenyl, and 3-hexenyl, and structural isomers thereof such as 2-methylallyl, and the like, of which vinyl and allyl are preferred.

The term "lower alkylene" means a divalent group of a straight or branched carbon chain having 1 to 6 carbon atoms, and its examples include methylene, ethylene, trimethylene, methylmethylene, methylethylene, dimethylmethylene, and the like.

The "cycloalkyl" means a monovalent group of a non-aromatic hydrocarbon ring having 3 to 8 carbon atoms, which may have a partial unsaturation, and its examples include cyclopropyl, cyclopentyl, cyclohexyl, cyclooctyl, cyclohexenyl, cyclooctandienyl, and the like.

The term "aryl" means a monovalent group of a mono- to tri-cyclic aromatic hydrocarbon ring having 6 to 14 carbon atoms, and its examples include phenyl, naphthyl, and the like, of which phenyl is preferred.

The term "aromatic heterocycle" means a monovalent group of a mono- to tri-cyclic aromatic ring having a hetero atom such as a nitrogen atom, an oxygen atom, a sulfur atom, and the like, and its examples include pyridyl, thienyl, furyl, benzimidazolyl, pyrazinyl, pyridazinyl, thiazolyl, pyrimidinyl, benzothiazoyl, pyrazolyl, indazolyl, pyrrolyl, oxazoyl, triazoyl, tetrazoyl, indolyl, quinolyl, isothiazolyl, isooxazoyl, imidazoyl, and the like, of which pyridyl is preferred.

The term "nonaromatic heterocycle" means a monovalent group of a five- to seven-membered ring having a hetero atom such as a nitrogen atom, an oxygen atom, a sulfur atom, and the like, which may have a partial unsaturation and may be condensed with an aryl or aromatic heterocycle, and its examples include pyrrolidinyl, imidazolydinyl, piperidinyl, piperazinyl, azepinyl, morphonyl, thiomorphonyl, tetrahydrofuryl, tetrahydrothienyl, and the like, of which pyrrolidinyl, tetrahydrofuryl, and tetrahydrothienyl are preferred.

The term "aromatic cyclic amino" means a monovalent group of a five- to seven-membered aromatic cyclic amine, which may contain a nitrogen, an oxygen, or a sulfur atom, and its examples include benzimidazolyl, indolyl, pyrazolyl, indazolyl, pyrrolyl, imidazolyl, and the like, of which pyrazolyl is preferred.

The term "nonaromatic cyclic amino" means a monovalent group of a three- to ten-membered, preferably a five- to seven-membered nonaromatic cyclic amine, which may have a partial unsaturation and comprise a nitrogen, an oxygen or a sulfur atom, and its examples include pyrrolidinyl, piperidinyl, azepinyl, morphonyl, thiomorphonyl, piperazinyl, pyrazolidinyl, indolinyl, isoindolinyl, dihydropyrrolyl, pyrrolinyl, dihydropyrrolinyl, and the like, of which pyrrolidinyl, piperidinyl, and dihydropyrrolyl are preferred.

The term "halogen" means a monovalent group of a halogen atom, and its examples include fluoro, chloro, bromo, iodo, and the like.

As the substituent group that can be used for the term "optionally substituted" or "which may be substituted", those which are commonly used as a substituent group for each corresponding group can be used, and each group may have one or more substituent groups.

In the definition of $R^1$, the "optionally substituted amino group" includes the groups represented by the above general Formulae (II) and (III).

As the substituent groups that can be used for "aryl, cycloalkyl, aromatic heterocycle, or nonaromatic heterocycle, each of which may be substituted" in the definition of $R^{12}$, and "optionally substituted nonaromatic cyclic amino group" and "optionally substituted aromatic cyclic amino group" in the definition of $R^{13}$, $R^{14}$, $R^3$, and $R^4$, the following groups (a) to (h) can be exemplified. $R^A$ is a lower alkyl group which may be substituted with one or more groups selected from the group consisting of —OH, —O-lower alkyl, an amino which may be substituted with one or two lower alkyls, a carbamoyl which may be substituted with one or two lower alkyls, an aryl, an aromatic heterocycle and a halogen.

(a) halogen;
(b) —OH, —O—$R^A$, —O-aryl, —OCO—$R^A$, oxo(=O);
(c) —SH, —S—$R^A$, —S-aryl, —SO—$R^A$, —SO-aryl, $SO_2$—$R^A$, —$SO_2$-aryl, sulfamoyl which may be substituted with one or two $R^A$;
(d) amino which may be substituted with one or two $R^A$, —NHCO—$R^A$c, —NHCO-aryl, —$NHSO_2$—$R^A$, —$NHSO_2$-aryl, nitro;
(e) —CHO, —CO—$R^A$, —$CO_2$H, —$CO_2$—$R^A$, carbamoyl which may be substituted with one or two $R^A$, cyano;
(f) aryl or cycloalkyl, each of which may be substituted with one or more groups selected from the group consisting of —OH, —O-lower alkyl, amino which may be substituted with one or two lower alkyls, carbamoyl which may be substituted with one or two lower alkyls, aryl, aromatic heterocycle, halogen and $R^A$;
(g) aromatic heterocycle or nonaromatic heterocycle, each of which may be substituted with one or more groups selected from the group consisting of —OH, —O-lower alkyl, amino which may be substituted with one or two lower alkyls, carbamoyl which may be substituted with one or two lower alkyls, aryl, aromatic heterocycle, halogen and $R^A$;
(h) lower alkyl or lower alkenyl, each of which may be substituted with one or more groups selected from the substituent groups described in (a) to (g).

As a protection group that can be used for "optionally protected hydrazino group" in the definition of $R^{23}$ and $R^{24}$, those which are commonly used as a protection group for an amino group can be used, and those described in "Protective Groups in Organic Synthesis", third edition, edited by Greene and Wuts, can be exemplified. Its examples include acetyl, methoxycarbonyl, ethoxycarbonyl, tert-butyloxycarbonyl, benzyloxycarbonyl, phthalimide, and the like, of which tert-butyloxycarbonyl is preferred.

The compound represented by the general Formula (I) may comprise asymmetric carbon atoms according to the kinds of substituent groups, and optical isomers based on the asymmetric carbon atom may exist. The compound of the present invention includes a mixture of these optical isomers or isolated ones. Also, tautomers may be included in the compound of the present invention, and the compound of the present invention includes these isomers as a mixture or as an isolated one.

In addition, the compound of the present invention may form a salt, which is included in the present invention as long as pharmaceutically acceptable. Examples of the salt include addition salts with a mineral acid such as hydrochloric acid, hydrobromic acid, hydroiodic acid, sulfuric acid, nitric acid, phosphoric acid, and the like, or an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, glutamic acid, and the like; salts with an inorganic base such as sodium, potassium, magnesium, calcium, and the like, or an organic base such as methylamine, ethylamine, ethanolamine, lysine, ornithine, and the like; and ammonium salts, and the like. And, a hydrate and a solvate of the compound and its pharmaceutically acceptable salt of the present invention, and those having polymorphism, are also included in the present invention. In addition, the compound of the present invention also includes a compound which is metabolized in a living organism to be converted into the compound of the general Formula (I) or the salt thereof, a so-called prodrug. As a group for forming the prodrug, those described in Prog. Med., 5; 2157–2161, 1985. and Hirokawa Shoten, 1990, "Development of medicine" Vol. 7, Molecular Design, pp 163–198 can be exemplified.

(Production Methods)

The compound and its pharmaceutically acceptable salt can be prepared by various known synthesis methods, using characteristics based on its basic backbone or the kinds of substituent groups. The Representative preparation methods will be explained in detail. And, according to the kinds of functional groups, it is advantageous in some cases in terms of preparation technique to substitute a functional group with a suitable protection group, i.e., a group that can be easily converted into the functional group, in the step of a preparation of raw material or intermediate. Then, if necessary, the protection group is removed to obtain a desired compound. Examples of the functional group include hydroxyl, carboxy, and amino groups, and examples of the protection group include those described in "Protective Groups in Organic Synthesis", third edition, edited by Greene and Wuts. It is preferable to suitably use them depending on reaction conditions.

<First Production Method>

(First step)

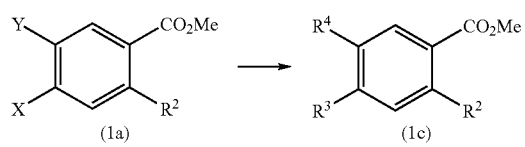

(wherein $R^2$, $R^3$, and $R^4$ are as defined in the foregoing; and one of X and Y is —H, a lower alkyl, or a halogen, and the other is a leaving group or an amino group.)

In this step, a leaving group of X or Y in the compound (1a) is substituted with an optionally substituted nonaromatic cyclic amine or aromatic cyclic amine ("(1b)") to prepare a compound (1c), or an amino group of X or Y is converted into a pyrrol-1-yl group. Examples of the leaving group of X or Y include a halogen atom, methylsulfonyl, 1H-benzotriazol-1-yloxy, methanesulfonyloxy, p-toluenesulfonyloxy, and trifluoromethanesulfonyloxy.

When one of $R^3$ and $R^4$ is pyrrole, one of X and Y is an amino group, and in this case, the compound (1c) can be synthesized with reference to J. Med. Chem., 28(10), 1405, 1985.

And, when X or Y is a leaving group, preferably I, Br, or trifluoromethanesulfonyloxy, the compound (1c) can be synthesized by a coupling reaction using Pd(0). The coupling reaction can be conducted with reference to Tetrahedron Letters, Vol. 38, No. 66, pp. 6359–662, 1997.

And, when X is a leaving group, preferably F or Cl, the compound (1c) can be synthesized by a substitution reaction. The reaction can be carried out free of a solvent or in an inert solvent including an aromatic hydrocarbon such as benzene, toluene, xylene, and the like; an ether such as diethylether, tetrahydrofuran (THF), dioxane, and the like; a halogenated hydrocarbon such as dichloromethane, 1,2-dichloroethane, chloroform, and the like; N,N-dimethylformamide (DMF); dimethylacetamide (DMA); N-methylpyrrolidone; dimethylsulfoxide (DMSO); an ester such as ethyl acetic acid (EtOAc); acetonitrile, and the like, or an alcohol solvent such as methanol (MeOH), ethanol (EtOH), 2-propanol, and the like, at room temperature or while heating under reflux, using equal moles of the compound (1a) and the compound (1b) or an excess amount of any one of them.

Depending on the compounds to be produced, it is advantageous to carry out the reaction in the presence of an organic base (preferably, triethylamine, diisopropylethylamine, N-methylmorpholin, pyridine, 4-(N,N-dimethylamino)pyridine), or a basic metal salt (preferably potassium carbonate, cesium carbonate, sodium hydroxide, or sodium hydride). And, when one of $R^3$ and $R^4$ is an optionally substituted pyrazolyl group, the substitution reaction may be carried out using an optionally protected hydrazine, preferably a hydrazine protected with mono tert-butyl oxycarbonyl instead of the compound (1b), and then, if necessary, the protection group is removed to react the aldehyde protected form of acylacetaldehyde (e.g., acetylacetaldehyde dimethylacetal) to form an optionally substituted pyrazol ring. The formation of the pyrazol ring is advantageously carried out in the presence of acid, preferably hydrochloric acid, trifluoroacetic acid, p-toluenesulfonic acid, and the like), under room temperature or with heating.

(Second step)

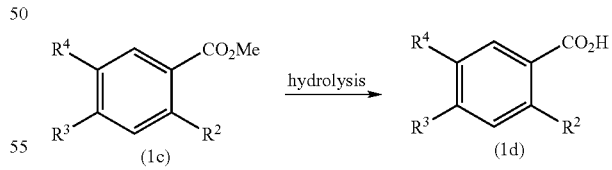

In this step, the compound (1c) obtained in the first step of the first production method is hydrolyzed to prepare a compound (1d).

The reaction can be carried out in a solvent inert to the compound (1c), such as an aromatic hydrocarbon, an ether, a halogenated hydrocarbon, an alcohol, DMF, DMA, DMSO, pyridine, water, and the like, in the presence of a mineral acid such as sulfuric acid, hydrochloric acid, hydrobromic acid, an organic acid such as formic acid, acetic acid, and the like, or a base such as sodium hydroxide, potassium hydroxide, potassium carbonate, sodium carbonate, cesium carbonate, or ammonia, under a cooling to a heat refluxing environment. Reaction temperature can be appropriately selected depending on the compounds.

(Third Step)

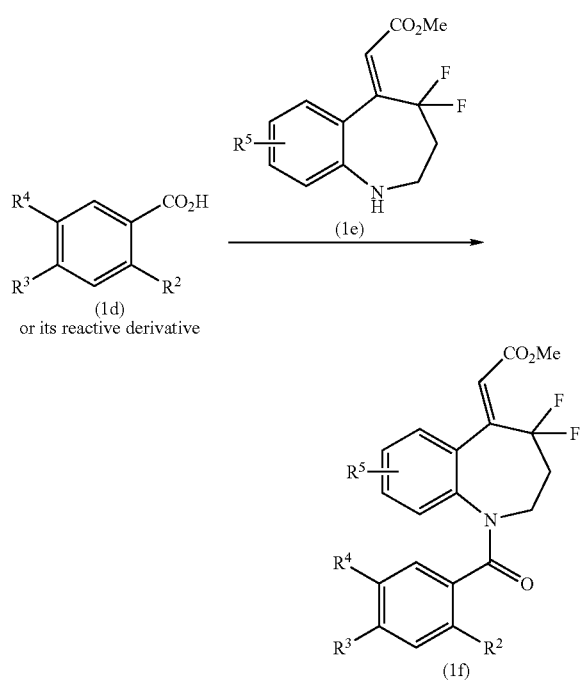

(wherein $R^5$ is as defined in the foregoing.)

In this step, a compound (1f) of the present invention is prepared by the amidation of the compound (1d) obtained in the second step of the first production method or its reactive derivative with a compound (1e).

As the reactive derivative of the compound (1d), a common ester such as methylester, ethylester, tert-butyl ester, and the like; an acid halide such as acid chloride, acid bromide, and the like; an acid azide; an active ester with N-hydroxybenzotriazole, p-nitrophenol, or N-hydroxysuccinimide, and the like; a symmetrical acid anhydride; an acid anhydride mixture of an alkyl halide carbonate, and the like, and an halocarboxylic acid alkylester, pivaloyl halide, p-toluenesulfonic acid chloride, and the like; and a phosphate-type acid anhydride mixture obtained by the reaction of diphenylphosphoryl chloride and N-methylmorpholin can be used.

And, when the compound (1d) is used in its free acid form or an active ester without isolation, it is preferable to use a condensing agent such as dicyclohexylcarbodiimide (DCC), 1,1'-carbonylbis-1H-imidazole(CDI), diphenylphosphorylazide (DPPA), diethylphosphorylcyanide, and 1-ethyl-3-(3-dimethylaminopropyl)carbodiimide hydrochloride (EDCI·HCl), and the like.

Particularly, in the present invention, an acid chloride method, a method of carrying out the reaction in the presence of both an active esterification agent and a condensing agent, or a method of treating a common ester with an amine is convenient because it is easy to prepare the compound of the present invention therewith. The reaction is, although it varies depending on the employed reactive derivative or condensing agent, carried out in an inert organic solvent such as a halogenated hydrocarbon, an aromatic hydrocarbon, an ether, an ester, acetonitrile, DMF, or DMSO, and the like, under a cooling, a cooling to room temperature, or a room temperature to heating environment.

In carrying out the reaction, in order to progress the reaction smoothly, it is advantageous in some cases to use the compound (1e) in an excess amount or to carry out the reaction in the presence of a base such as N,N-dimethylaniline, pyridine, 4-(N,N-dimethylamino)pyridine, picoline, lutidine, and the like. And, a salt consisting of a strong acid and a weak base such as pyridine hydrochloride, pyridine, p-toluenesulfonate, N,N-dimethylaniline hydrochloride, and the like can be used. Pyridine can also be used as a solvent.

Particularly, it is preferable to carry out the reaction in a solvent such as acetonitrile, DMF, and the like, in the presence of a base such as pyridine, N,N-dimethylaniline, and the like, or a salt such as pyridine hydrochloride, and the like.

(Fourth step)

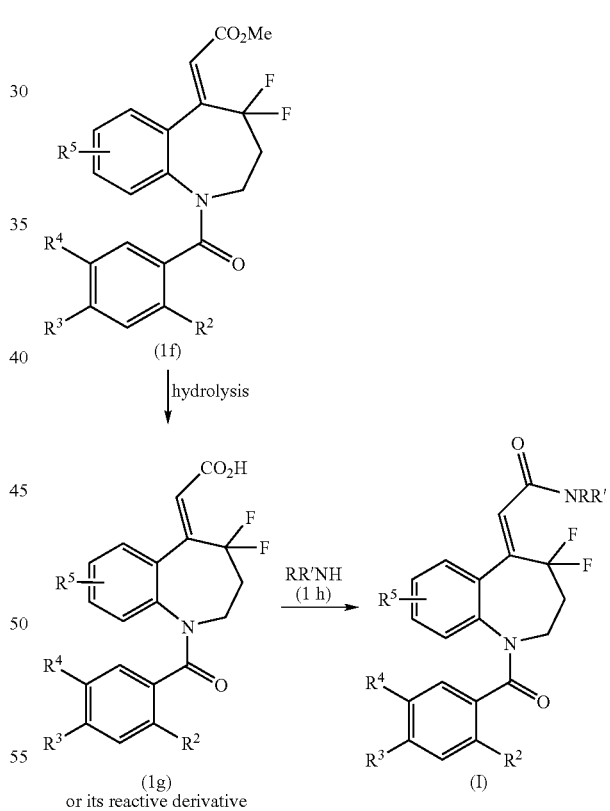

In this step, a compound (1f) of the present invention obtained in the third step of the first production method is hydrolyzed to prepare a compound (1g) of the present invention, and then the compound (I) of the present invention is prepared by the amidation of the compound (1g) or its reactive derivative with a compound (1h).

Each reaction can be carried out in accordance with the second step or third step of the first production method.

<Second Production Method>

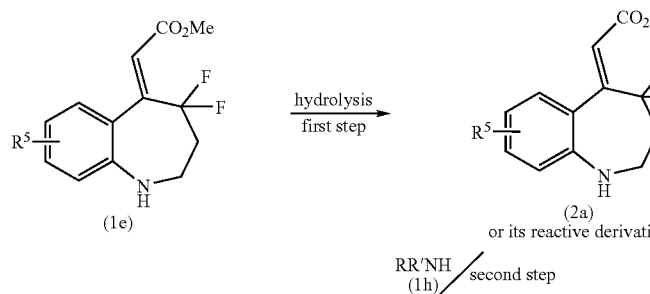

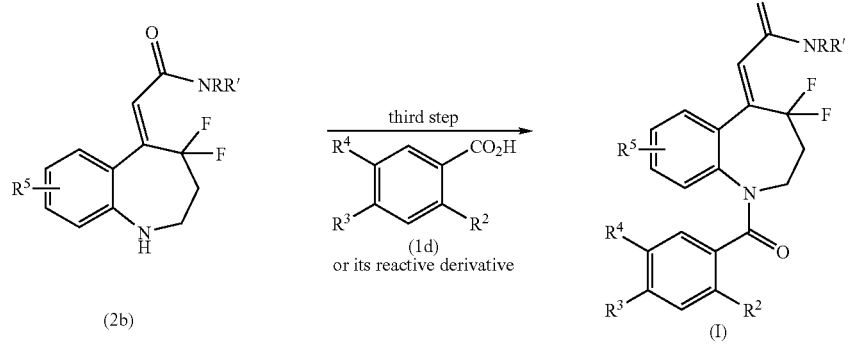

In this method, a compound (1e) is hydrolyzed in a first step to prepare a compound (2a), a compound (2b) is prepared by the amidation of the compound (2a) or its reactive derivative with a compound (1 h) in a second step, and then the compound (I) is prepared by the amidation of the compound (2b) with a compound (1d) or its reactive derivative in a third step.

The reaction in the first step can be carried out in accordance with the second step of the first production method, and the reactions in the second and third steps in accordance with the third step of the first production method.

<Third Production Method>

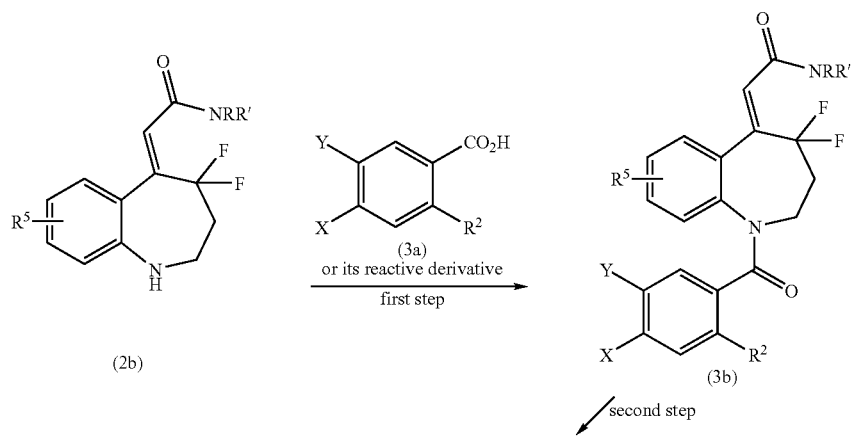

-continued

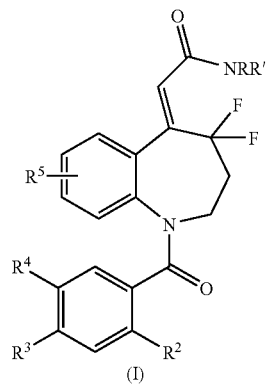

(I)

In this method, a compound (3b) is prepared by the amidation of the compound (2b) obtained in the second step of the second production method with a compound (3a) or its reactive derivative in a first step, and in a second step, a leaving group of X or Y of the obtained compound (3b) is substituted with a compound (1b) or an optionally substituted hydrazine to form an optionally substituted pyrazole ring, as shown in the first step of the first production method, thereby forming a compound (I) of the present invention. The leaving group of X or Y is as defined in the first step of the first production method.

The reaction in the first step can be carried out in accordance with the third step of the first production method, and the reaction in the second step in accordance with the first step of the first production method.

<Fourth Production Method>

-continued

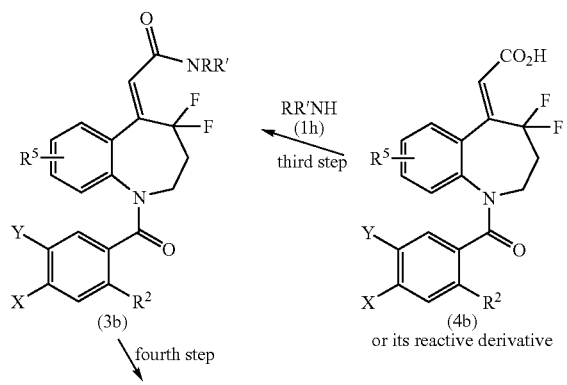

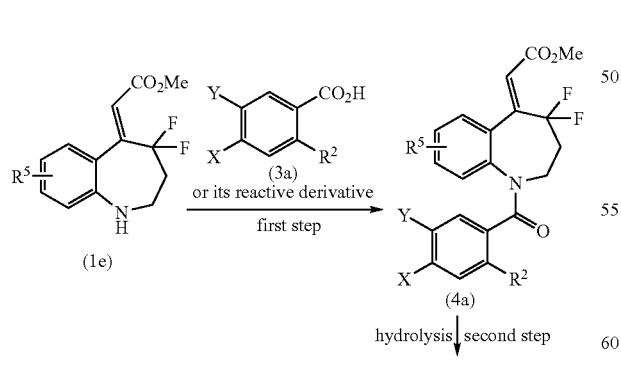

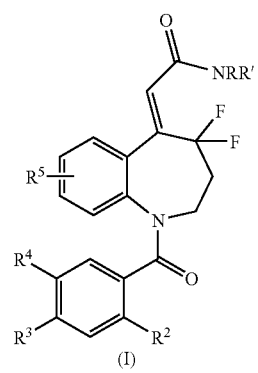

(I)

In this method, a compound (4a) is prepared by the amidation of a compound (1e) with a compound (3a) or its reactive derivative in a first step, the obtained compound (4a) is hydrolyzed to prepare a compound (4b) in a second step, and a compound (3b) is prepared by the amidation of the obtained compound (4b) or its reactive derivative with a compound (1h) in a third step, and then, in a fourth step, the leaving group of X or Y of the obtained compound (3b) is substituted with a compound (1b) or an optionally substituted hydrazine to form an optionally substituted pyrazole ring, as shown in the first step of the first production method, thereby preparing a compound (I) of the present invention. The leaving group of X or Y is as defined in the first step of the first production method.

The reactions in the first and third steps can be carried out in accordance with the third step of the first production method, the reaction in the second step in accordance with the second step of the first production method, and the reaction in the fourth step in accordance with the first step of the first production method.

<Fifth Production Method>

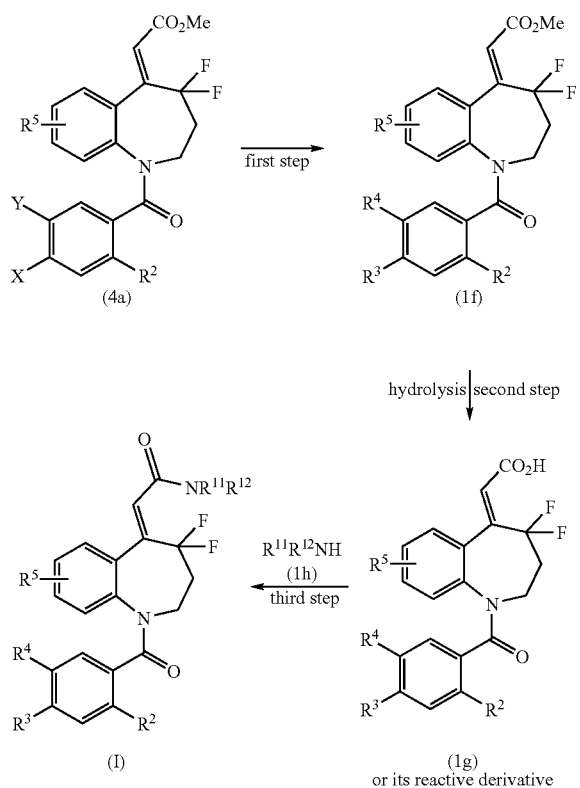

In this method, in a first step, the leaving group of X or Y of the compound (4a) obtained in the first step of the fourth production method is substituted with a compound (1b) or an optionally substituted hydrazine to form an optionally substituted pyrazole ring, as shown in the first step of the first production method, thereby forming a compound (1f) of the present invention, which is hydrolyzed to prepare a compound (1g) of the present invention in a second step, and then the compound (I) of the present invention is prepared by the amidation of the compound (1g) or its reactive derivative with a compound (1h) in a third step. The leaving group of X or Y is as defined in the first step of the first production method.

The reaction in the first step can be carried out in accordance with the first step of the first production method, the reaction in the second step in accordance with the second step of the first production method, and the reaction in the third step in accordance with the third step of the first production method.

The thus produced compound of the present invention is isolated and purified as its free form or as a salt thereof. A salt of the compound (I) can be produced by subjecting it to a usual salt formation reaction. The isolation and purification are carried out by usual chemical manipulations such as extraction, concentration, evaporation, crystallization, filtration, recrystallization, various types of chromatography, and the like.

Various types of isomers can be separated by usual method using the difference in physicochemical properties among isomers. For example, racemic compounds can be separated by a general racemic compound resolution method, e.g., a method in which racemic compounds are converted into diastereomer salts with an optically active base such as tartaric acid, and the like and then subjected to optical resolution. And, diastereomers can be separated by fraction crystallization or various types of chromatography or the like. Also, optically active compounds can be prepared using appropriate optically active starting materials.

The compound and its salt of the present invention have excellent stimulation effects for arginine vasopressin $V_2$ receptors. Thus, the compound of the present invention has antidiuretic effects and effects of releasing blood coagulating agents VIII factor and von Willebrand factor, is useful for treating various urination disorders, polyuria, or hemorrhage conditions, and is effective in the diagnosis, prevention, and treatment of polyuria, urinary incontinence, central diabetes insipidus, nocturia, nocturnal enuresis, spontanous hemorrhage, hemophilia, von Willebrand disease, uremia, congenital or acquired platelet dysfunction, traumatic or surgical hemorrhage, hepatocirrhosis, and the like.

Since the compound of the present invention has little inhibition effects against medicine metabolism enzymes CYP3A4 and CYP2C9, there is less concern for interaction with other medicines metabolized by CYP3A4 or CYP2C9, compared with known benzazepine derivatives having arginine vasopressin $V_2$ receptor agonist effects, and it can be safely used in combined therapy with various preparations.

Examples of medicines metabolized by CYP3A4 include simvastatin, lovastatin, fluvastatin, midazolam, niphedipine, amlodipine, nicardipine, and the like, and example of medicines metabolized by CYP2C9 include diclofenac, ibuprofen, indomethacin, tolbutamide, glibenclamide, losartan, and the like (General Clinic, 48(6), 1427–1431, 1999).

Pharmaceutical efficacy of the compound of the present invention was confirmed by the following assays.

(1) $V_2$ Receptor Binding Assay

A human $V_2$ expression CHO cell membrane sample was prepared in accordance with a method of Tahara, et al. (British Journal of Pharmacology. Vol 125, p. 1463–1470, 1998). 2 μg of the membrane sample were incubated in a total of 250 μl of 50 mM tris-chloric acid buffer solution (pH=7.4) containing 10 mM $MgCl_2$ and 0.1% bovine serum albumin (BSA), together with [$^3$H]-Arginine-Vasopressin (hereinafter referred to as '[$^3$H]-Vasopressin') (0.5 nM, Specific activity=75 Ci mmol) and a test compound ($10^{-10}$~$10^{-5}$ M) at 25° C. for 60 minutes. Then, free [$^3$H]-Vasopressin and receptor binding [$^3$H]-Vasopressin were separated using a cell harvester, and the receptor binding [$^3$H]-Vasopressin was adsorbed on a Unifilter Plate GF/B glass filter, sufficiently dried, and then mixed with a microplate scintillation cocktail. The amount of receptor binding [$^3$H]-Vasopressin was measured using a top count, and inhibition rate was calculated by the following equation.

Inhibition Rate(%)=100−($C_1$−$B_1$)/($C_0$−$B_1$)×100

$C_1$: the amount of [$^3$H]-Vasopressin bound to the membrane sample, when the receptor membrane sample is treated in the coexistence of a test compound of known concentration and [$^3$H]-Vasopressin $C_0$: the amount of [$^3$H]-Vasopressin bound to the membrane sample, when the receptor membrane sample is treated with [$^3$H]-Vasopressin, in the absence of a test compound $B_1$: the amount of [$^3$H]-Vasopressin bound to the membrane sample, when the receptor membrane sample is treated in the coexistence of an excess amount of Vasopressin ($10^{-6}$ M) and [$^3$H]-Vasopressin From the above equation, concentration of the test compound corresponding to the inhibition rate of 50% ($IC_{50}$) was calculated, from which affinity of the test compound for a receptor, i.e., dissociation coefficient (Ki) was calculated by the following equation.

Dissociation Coefficient (Ki)=$IC_{50}$/(1+[L]/Kd)

[L]: the concentration of [$^3$H]-Vasopressin
Kd: dissociation coefficient of [3H]-Vasopressin for the receptor, calculated from saturation binding assay

TABLE 1

[Affinity for $V_2$ receptor]

| Compound | Ki (nM) | Compound | Ki (nM) |
|---|---|---|---|
| Example 72 | 3.7 | Example 58 | 4.8 |
| Example 76 | 2.2 | Example 74 | 5.6 |
| Example 119 | 5.6 | Control | 68 |

As the control, the compound of Example 32 described in WO 97/22591 (Compound name: 2-[(5R)-1-(2-chloro-4-pyrrolidin-1-ylbenzoyl)-2,3,4,5-tetrahydro-1H-1-benzazepin-5-yl]-N-isopropyacetamide) was used.

As shown in Table 1, it has been verified that the compound of the present invention has high affinity for the $V_2$ receptor.

(2) Antidiuresis Assay (Intravenous Administration)

For the assay, 5 Wistar male rats (10~12 weeks of age) were employed for each group. For group A, 0.3 mg/kg of the compound of Example 135, for group B, 0.3 mg/kg of the compound of Example 201, and for group C, 1 ml/kg of physiological saline solution comprising DMSO as a control were intravenously administrated. After 15 minutes, 30 ml/kg of distilled water were orally administrated (water load). Until 2 hours after the water load, urine was collected in a metabolism cage, and the amount of urine when the water load is set to 100% was calculated as the urinary excretion rate. For the assay, the average value in each group of urinary excretion rate until 1 hour after the water load and that until 2 hours after the water load was employed. The results are described in the following Table 2.

TABLE 2

[Antidiuretic effects (intravenous administration)]

| | | Urinary excretion rate (%) | |
|---|---|---|---|
| | Compound | After 1 hour | After 2 hours |
| Group A | Example 135 | 0 | 1.1 |
| Group B | Example 201 | 0 | 13.3 |
| Group C | DMSO | 49.9 | 58.4 |

As shown in Table 2, it has been verified that the compound of the present invention has excellent antidiuretic effects.

(3) Antidiuresis Assay (Oral Administration)

For the assay, Wistar male rats (10~12 weeks of age) were employed. The test compound was orally administrated, and after 15 minutes, 30 ml/kg of distilled water were orally administrated (water load). Until 4 hours after the water load, urine was collected in a metabolism cage, and the amount of urine when the water load was set to 100% was calculated as the urinary excretion rate. For the assay, the amount of the test compound required for decreasing urinary excretion rate by 50% ($ED_{50}$) was employed. The results are described in the following Table 3.

TABLE 3

[Antidiuretic effects (oral administration)]

| Compound | $ED_{50}$ (mg/kg) | Compound | $ED_{50}$ (mg/kg) |
|---|---|---|---|
| Example 139 | 0.14 | Example 174 | 0.17 |
| Example 76 | 0.22 | Example 173 | 0.16 |
| Example 175 | 0.38 | | |

As shown in Table 3, it has been verified that the compound of the present invention has excellent antidiuretic effects by oral administration as well as by intravenous administration.

(4) Cytochrome P450 (3A4) Enzyme Inhibition Assay

The assay was carried out in accordance with a method of Crespi, et al. (Analytical Biochemistry, 248, 188–190, 1997).

A 96 well plate was employed, and 7-benzyloxy-4-(trifluoromethyl)coumarin ($5\times10^{-5}$ M) as a substrate, a test compound ($4.9\times10^{-8}$~$5\times10^{-5}$ M), and an enzyme ($5\times10^{-9}$ M) were incubated in a total of 200 μl of a 200 mM phosphate buffer solution (pH=7.4) comprising 8.2 μM NADP+, 0.41 mM glucose-6-phosphate, 0.41 mM $MgCl_2$, and 0.4 Units/ml glucose-6-phosphate dehydrogenase, at 37° C. for 30 minutes. Then, 0.5 M aqueous solution of 2-amino-2-hydroxymethyl-1,3-propanediol containing 80% acetonitrile was added thereto to stop the reaction, and fluorescence intensity was measured with a fluorescent plate reader (excited wavelength: 409 nm, fluorescent wavelength: 530 nm). Inhibition rate was calculated by the following equation, and the concentration of the test compound corresponding to an inhibition rate of 50% ($IC_{50}$) was calculated. The results are described in the following Table 4.

Inhibition Rate (%)=100−($C_1$−$B_1$)/($C_0$−$B_1$)×100

$C_1$: fluorescence intensity in the presence of a known concentration of test compound, enzyme, and a substrate
$C_0$: fluorescence intensity in the presence of an enzyme and a substrate, in the absence of a test compound $B_1$: fluorescence intensity of a blank well (5) Cytochrome P450 (2C9) Enzyme Inhibition Effects The assay was carried out in accordance with a method of Crespi, et al. (Analytical Biochemistry, 248, 188–190, 1997).

A 96 well plate was employed, and 7-methoxy-4-(trifluoromethyl)coumarin ($7.5 \times 10^{-5}$ M) as a substrate, a test compound ($4.9 \times 10^{-8} \sim 5 \times 10^{-5}$ M), and an enzyme ($10^{-8}$ M) were incubated in a total of 200 µl of a 200 mM phosphate buffer solution (pH=7.4) comprising 8.2 µM NADP+, 0.41 mM glucose-6-phosphate, 0.41 mM $MgCl_2$, and 0.4 Units/ml glucose-6-phosphate dehydrogenase, at 37° C. for 45 minutes. Then, 0.5 M aqueous solution of 2-amino-2-hydroxymethyl-1,3-propanediol containing 80% acetonitrile was added thereto to stop the reaction, and fluorescence intensity was measured with a fluorescent plate reader (excited wavelength: 409 nm, fluorescent wavelength: 530 nm). Inhibition rate was calculated from the above equation in (4), and the concentration of the test compound corresponding to an inhibition rate of 50% ($IC_{50}$) was calculated. The results are described in the following Table 4.

TABLE 4

[CYP(3A4 and 2C9) inhibition effects]

| Compound | $IC_{50}$ (µM) | |
| --- | --- | --- |
| | CYP3A4 | CYP2C9 |
| Example 8 | >20 | 13 |
| Example 190 | 16 | 6.5 |
| Example 220 | 10 | 11 |
| Control | <0.091 | <0.091 |

As shown in Table 4, the compound of the present invention showed very low inhibition effects for the medicine metabolism enzymes CYP3A4 and CYP2C9. The control was the same as in Table 1.

A pharmaceutical composition of the present invention can be prepared by generally used methods using one or more kinds of the compound of the present invention and pharmaceutical carriers, fillers, and other additives generally used in the preparation of medicaments.

It may be administrated either by oral administration through tablets, pills, capsules, granules, powders, solutions, and the like, or by parenteral administration through injections such as intravenous injection, intramuscular injection, and the like, or through suppositories, or pernasal, permucosal, or percutaneous preparations, and the like.

The solid composition for use in the oral administration according to the present invention is used in the forms of tablets, powders, granules, and the like. In such a solid composition, one or more active substances are mixed with at least one inert diluent such as lactose, mannitol, glucose, hydroxypropylcellulose, microcrystalline cellulose, starch, polyvinyl pyrrolidone, metasilicate, or magnesium aluminate. In the usual way, the composition may contain additives other than the inert diluent, which include a lubricant such as magnesium stearate, a disintegrating agent such as calcium cellulose glycolate, a stabilizing agent such as lactose, and a solubilization-assisting agent such as glutamic acid or aspartic acid. As occasion demands, tablets or pills may be coated with a sugar coat or a film of gastrosoluble or enterosoluble substance such as sucrose, gelatin, hydroxypropylcellulose, hydroxypropylmethylcellulose phthalate, or the like.

The liquid composition for oral administration includes pharmaceutically acceptable emulsions, solutions, suspensions, syrups, elixirs, and the like, and it contains a generally used inert diluent such as purified water or ethanol. In addition to the inert diluent, this composition may also contain auxiliary agents such as a moistening agent and a suspending agent, as well as a sweetener, a flavoring agent, an aromatic, and an antiseptic.

The injections for parenteral administration include aseptic aqueous or non-aqueous solutions, suspensions, and emulsions. Examples of the aqueous solutions and suspensions include distilled water for injection use, and physiological saline. Examples of the non-aqueous solutions and suspensions include plant oil such as propylene glycol, polyethylene glycol, olive oil or the like, alcohol such as ethanol, polysorbate 80 (trade name), and the like. Such a composition may further contain auxiliary agents such as an antiseptic, a moistening agent, an emulsifying agent, a dispersing agent, a stabilizing agent (e.g., lactose), and a solubilization-assisting agent (e.g., glutamic acid or aspartic acid. These compositions are sterilized, for example by filtration through a bacteria retaining filter, blending of a germicide, or irradiation. Alternatively, they may be used by firstly making into sterile solid compositions and dissolving them in sterile water or a sterile solvent for injection use, prior to their use.

In the case of oral administration, a daily dose is approximately 0.0001~50 mg/kg of body weight, preferably approximately 0.001~10 mg/kg, and more preferably approximately 0.01~1 mg/kg, and the daily dose is administered once a day or by dividing it into 2 to 4 doses per day. In the case of intravenous administration, a daily dose is approximately 0.0001~1 mg/kg of body weight, preferably approximately 0.0001~0.1 mg/kg, and the daily dose is administered once a day or by dividing it into plural doses per day. The dose is appropriately determined by taking symptoms, age, the sex of the patient to be treated, and the like into consideration. Since the dose is varied depending on various conditions, a smaller dose is sufficient in some cases.

BEST MODE FOR CARRYING OUT THE INVENTION

The following describes the invention more illustratively with reference to examples, but the present invention is not limited to these examples. In this connection, novel materials are included in the starting materials to be used in the examples, and production methods of the starting materials from known materials are described as reference examples.

REFERENCE EXAMPLE 1

20.85 g of methyl 2-chloro-4-fluorobenzoate were dissolved in 150 ml of N-methylpyrrolidone, 30.68 g of potassium carbonate and 9.38 ml of 3-methylpyrazole were added thereto, and the mixture was stirred at 120° C. for 3 hours. Additionally, thereto was added 1.79 ml of 3-methylpyrazole, and the mixture was stirred at 120° C. for 3 hours. The reaction solution was cooled, mixed with water, and extracted with EtOAc. The organic layer was washed with water and brine, and then dried over magnesium sulfate. The solvent was evaporated, and then the residue was purified by silica gel column chromatography (hexane-EtOAc (20:1)) to obtain 9.25 g of methyl 2-chloro-4-(3-metyl-1H-pyrazol-1-yl)benzoate.

The compounds of Reference Examples 2–40 were synthesized in the same manner as described in Reference Example 1.

REFERENCE EXAMPLE 41

2.0 g of methyl 4-amino-2-chlorobenzoate were dissolved in 10 ml of acetic acid, 2.0 ml of 2,5-dimethoxytetrahydrofuran were added thereto, and the mixture was heated under reflux for 15 minutes. After cooling the reaction solution, the solvent was evaporated. The obtained residue was mixed with EtOAc and saturated NaHCO₃ aq. and extracted. The organic layer was washed with brine, and dried over sodium sulfate anhydride. After evaporating the solvent, the residue was purified by silica gel column chromatography (hexane-EtOAc (4:1)) to obtain 2.1 g of methyl 2-chloro-4-(1H-pyrrol-1-yl)benzoate.

The compound of Reference Example 42 was synthesized in the same manner as described in Reference Example 41.

REFERENCE EXAMPLE 43

2.0 g of methyl 4-bromo-2-methylbenzoate were dissolved in 20 ml of toluene, and 1.08 ml of pyrrolidine, 4.0 g of cesium carbonate, 200 mg of tris(dibenzylideneacetone)-dipalladium (0) and 200 mg of (R)-(+)-2,2'-bis(diphenylphosphino)-1,1'-binaphthyl were added thereto, and then the mixture was heated under reflux for 6 hours. The reaction solution was cooled, mixed with water and EtOAc, and extracted. The organic layer was washed with water and brine, and dried over anhydrous sodium sulfate. After evaporating the solvent, the residue was purified by silica gel column chromatography (hexane-EtOAc (25:1)) to obtain 0.784 g of methyl 2-methyl-4-pyrrolidin-1-ylbenzoate.

The compound of Reference Example 44 was synthesized in the same manner as described in Reference Example 43.

REFERENCE EXAMPLE 45

9.25 g of the compound of the Reference Example 1 were dissolved in 10 ml of acetic acid and 10 ml of 6M HCl aq., and then the mixture was heated under reflux for 13 hours. The reaction solution was cooled, and then poured into ice water, and the thus precipitated crystals were collected by filtration to obtain 8.56 g of 2-chloro-4-(3-methylpyrazol-1-yl) benzoic acid.

REFERENCE EXAMPLE 46

10.7 g of the compound of Reference Example 2 were dissolved in 60 ml of MeOH and 20 ml of 5M NaOH aq., and the mixture was heated under reflux for 2 hours. The reaction solution was cooled, and then neutralized with 2M HCl aq., and the solvent was evaporated. To the obtained residue, water was added, and the thus precipitated crystals were collected by filtration to obtain 10.17g of 2-chloro-4-pyrrolidin-1-ylbenzoic acid.

The compounds of Reference Examples 47–88 were synthesized in the same manner as described in Reference Example 46.

The structures and physical data of the compounds of Reference Examples are shown in Tables 5 to 8. Symbol meanings in the Tables are as follows.

Rf: Reference Example number

MS: Mass spectrometry data (FAB-MS(M+H)⁺ unless otherwise noted, and MM, MN, and ME respectively indicate FAB-MS(M)⁺, FAB-MS(M−H)⁺, and EI-MS(M)⁺).

$R^b$, $R^c$, $R^d$: substituent group in the general formula (Me: methyl, Et: ethyl, iPr: isopropyl, cPr: cyclopropyl, tBu: tert-butyl, Ph: phenyl, pra: pyrazolyl, pyrr: pyrrolinidyl, mor: morpholinyl, the: thienyl, imid: imidazolyl, bimid: benzoimidazolyl, pipe: piperidyl, di: di), The number before the substituent group indicates location of substitution. Thus, for example, 3-Me-1-pra indicates 3-methylpyrazol-1-yl, 3,3-diMe-1-pyrr indicates 3,3-dimethylpyrrolidin-1-yl, and 3-(2-the)-1-pra indicates 3-thiophene-2-ylpyrazol-1-yl.

TABLE 5

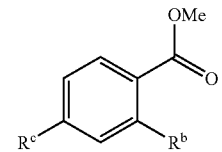

| Rf | $R^b$ | $R^c$ | MS |
|---|---|---|---|
| 1 | Cl | 3-Me-1-pra | 251. |
| 2 | Cl | 1-pyrr | 240. |
| 3 | Cl | 1-pra | 237. |
| 4 | Cl | 4-mor | ME:255. |
| 5 | Cl | 3-Ph-1-pra | 313. |
| 6 | Cl | 4-Br-1-pra | 315,317. |
| 7 | Cl | 3-(2-the)-1-pra | 319. |
| 8 | Cl | indazol-1-yl | 287. |
| 9 | Cl | 3,5-diMe-1-pra | 265. |
| 10 | Cl | 2-Me-imid | 251. |
| 11 | Cl | 1-bimid | 287. |
| 12 | Cl | 5-Me-1-pra | 251. |
| 13 | Cl | 2-Me-1-pyrr | 254. |
| 14 | Cl | 3-(R)—Me-1-pyrr | 254. |
| 15 | Cl | 3-(S)—Me-1-pyrr | 254. |
| 16 | Cl | 3,3-diMe-1-pyrr | MM:267. |
| 17 | Cl | 3-F-1-pyrr | 258. |
| 18 | Cl | 3-Ph-1-pyrr | 316. |
| 19 | Cl | 3-Me-3-Et-1-pyrr | 282. |
| 20 | Cl | 3,5-diMe-1-pipe | 282. |
| 21 | Cl | 3-Me-1-pipe | 268. |
| 22 | Cl | 3-Et-1-pra | 265. |
| 23 | Cl | 3-iPr-1-pra | 279. |
| 24 | Cl | 3-cPr-1-pra | 277. |
| 25 | CF₃ | 1-pyrr | 274. |
| 26 | CF₃ | 3-Me-1-pra | 285. |
| 27 | CF₃ | 3-(R)—Me-1-pyrr | 288. |
| 28 | CF₃ | 3-(S)—Me-1-pyrr | 288. |
| 29 | CF₃ | 3,4-diMe-1-pyrr | 302. |
| 30 | CF₃ | 3,3-diMe-1-pyrr | MM:301. |
| 31 | CF₃ | 2,5-dihydropyrrol-1-yl | 272. |
| 32 | CF₃ | 3-iPr-1-pra | 313. |
| 33 | CF₃ | 3-F₃C-1-pra | 339. |
| 34 | CF₃ | 3,5-diMe-1-pra | 299. |
| 35 | CF₃ | 4-Me-1-pra | 285. |
| 36 | CF₃ | 3-tBu-1-pra | 327. |
| 37 | CF₃ | 5-Me-1-pra | 285. |
| 39 | Cl | 1-pipe | ME:253. |
| 40 | Cl | azepin-1-yl | ME:267. |
| 41 | Cl | pyrrol-1-yl | 236. |
| 42 | Cl | 2,5-diMe-pyrrol-1-yl | MM:263. |
| 43 | Me | 1-pyrr | 220. |

TABLE 6

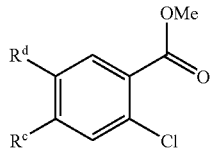

| Rf | R$^c$ | R$^d$ | MS |
|---|---|---|---|
| 38 | 3-Me-1-pra | F | 269. |
| 44 | H | 1-pyrr | 240. |

TABLE 7

| Rf | R$^b$ | R$^c$ | MS |
|---|---|---|---|
| 45 | Cl | 3-Me-1-pra | MN:235. |
| 46 | Cl | 1-pyrr | 226. |
| 47 | Cl | 1-pra | 223. |
| 48 | Cl | 4-mor | MN:241. |
| 49 | Cl | 3-Ph-1-pra | MN:297. |
| 50 | Cl | 4-Br-1-pra | MN:299,301. |
| 51 | Cl | 3-(2-the)-1-pra | MN:303. |
| 52 | Cl | indazol-1-yl | MN:271. |
| 53 | Cl | 3,5-diMe-1-pra | MN:249. |
| 54 | Cl | pyrrol-1-yl | MN:220. |
| 55 | Cl | 2-Me-1-imid | 237. |
| 56 | Cl | 1-bimid | 273. |
| 57 | Cl | 5-Me-1-pra | MN:235. |
| 58 | Cl | 2-Me-1-pyrr | 240. |
| 59 | Cl | 3-(R)—Me-1-pyrr | 240. |
| 60 | Cl | 3-(S)—Me-1-pyrr | 240. |
| 61 | Cl | 3,3-diMe-1-pyrr | 254. |
| 62 | Cl | 3-F-1-pyrr | 244. |
| 63 | Cl | 3-Ph-1-pyrr | MN:300. |
| 64 | Cl | 3-Me-3-Et-1-pyrr | 268. |
| 65 | Cl | 3,5-diMe-1-pipe | MN:266. |
| 66 | Cl | 3-Me-1-pipe | MN:252. |
| 67 | Cl | 3-Et-1-pra | 251. |
| 68 | Cl | 3-iPr-1-pra | 265. |
| 69 | Cl | 3-cPr-1-pra | 263. |
| 70 | Cl | 2,5-diMe-pyrrol-1-yl | MN:248. |
| 71 | CF$_3$ | 1-pyrr | 258. |
| 72 | CF$_3$ | 3-Me-1-pra | 271. |
| 73 | CF$_3$ | 3-(R)—Me-1-pyrr | 274. |
| 74 | CF$_3$ | 3-(S)—Me-1-pyrr | MN:272. |
| 75 | CF$_3$ | 3,4-diMe-1-pyrr | 288. |
| 76 | CF$_3$ | 3,3-diMe-1-pyrr | 288. |
| 77 | CF$_3$ | 2,5-dihydropyrrol-1-yl | 258. |
| 78 | CF$_3$ | 3-iPr-1-pra | 299. |
| 79 | CF$_3$ | 3-F$_3$C-1-pra | MN:323. |
| 80 | CF$_3$ | 3,5-diMe-1-pra | 285. |
| 81 | CF$_3$ | 4-Me-1-pra | 271. |
| 82 | CF$_3$ | 3-tBu-1-pra | 313. |
| 83 | CF$_3$ | 5-Me-1-pra | 271. |
| 84 | Me | 1-pyrr | 206. |
| 85 | Cl | 1-pipe | MN:238. |
| 86 | Cl | azepin-1-yl | MN:252. |

TABLE 8

| Rf | R$^c$ | R$^d$ | MS |
|---|---|---|---|
| 87 | 3-Me-1-pra | F | 255. |
| 88 | H | 1-pyrr | 226. |

REFERENCE EXAMPLE 89

8.0 g of methyl (2Z)-(4,4-difluoro-1,2,3,4-tetrahydro-5H-1benzazepin-5-ylidene)acetate were dissolved in 20 ml of MeOH and 20 ml of THF. 45 ml of 1M NaOH aq. were added thereto, and the mixture was stirred at room temperature for 15 hours. The reaction solution was concentrated under reduced pressure, and the residue was neutralized with 1M HCl aq. The reaction solution was mixed with chloroform and extracted. The organic layer was washed with brine, dried over sodium sulfate, and the solvent was evaporated to obtain 4.57 g of carboxylic acid intermediate. 4.57 g of the carboxylic acid intermediate were dissolved in 45 ml of DMF. 2.22 ml of 2-picolyl amine, 3.6 g of 1-hydroxybenzoimidazol (HOBt), and 5.6 g of 1-ethyl-3-(3'-dimethylaminopropyl)carbodiimide hydrochloride (EDCI.HCl) were added thereto, and the mixture was stirred at room temperature for 18 hours. The reaction solution was mixed with water and EtOAc and extracted therewith. The organic layer was washed with brine, and dried over sodium sulfate anhydride. After evaporation of the solvent, the residue was purified by silica gel column chromatography (chloroform-MeOH (25:1)) to obtain 6.849 g of (2Z)-2-(4,4-difluoro-1,2,3,4-tetrahydro-5H-1-benzazepin-5-ylidene)-N-(pyridine-2-ylmethyl)acetamide.

FAB-MS; 330. ([M+H]$^+$)

REFERENCE EXAMPLE 90

To a solution of 1.37 g of the compound of Example 6, 0.45 g of HOBt, and 0.63 g of EDCI.HCl in 15 ml of DMF, 0.46 g of sarcosinic methylester hydrochloride and 0.47g of triethylamine were added, and the mixture was stirred at room temperature overnight. The reaction solution was mixed with NaHCO$_3$ aq. and EtOAc and extracted. The organic layer was washed with water and brine, and dried over anhydrous magnesium sulfate. After evaporation of the solvent, the obtained ester intermediate was dissolved in 20 ml of MeOH, 5 ml of 1M NaOH aq. was added thereto, and the mixture was stirred at room temperature for 1 hour. To the crude product obtained by the evaporation of the solvent, 1M HCl aq. was added, and the thus precipitated white crystals were collected by filtration, washed with water, and dried under reduced pressure to obtain 1.43 g of [(((2Z)-2-{1-[2-chloro-4-(3-methyl-1H-pyrazol-1-yl)benzoyl]-4,4-difluoro-1,2,3,4-tetrahydro-5H-1-benzazpine-5-ylidene}acetyl(methyl)amino)acetic acid.

FAB-MS; 529. ([M+H]$^+$)

EXAMPLE 1

To a suspension of 21.0 g of 2-chloro-4-(3-methyl-1H-pyrazol-1-yl)benzoic acid in 200 ml of 1,2-dichloroethane, 15 ml of thionyl chloride and 3 drops of DMF were added at room temperature, and the mixture was stirred at 70° C. for 2 hours. The reaction solution was cooled to room temperature, the solvent was evaporated, and the residue was dried to obtain acid chloride form. 22.5 g of methyl (2Z)-(4,4-difluoro-1,2,3,4-tetrahydro-5H-1-benzazepin-5-ylidene)acetate were added thereto, 200 ml of pyridine was added thereto under ice cooling, and the mixture was stirred at room temperature for 20 hours. After completion of the reaction, the solvent was evaporated, and the residue was mixed with diluted hydrochloric acid water and EtOAc and extracted. The organic layer was washed with brine, and dried over anhydrous magnesium sulfate. After evaporation of the solvent, the residue was purified by silica gel column chromatography (hexane-EtOAc (9:1~4:1)) to obtain 38.0 g of methyl (2Z)-{1-[2-chloro-4-(3-methyl-1H-pyrazol-1-yl)benzoyl]-4,4-difluoro-1,2,3,4-tetrahydro-5H-1-benzazepin-5-ylidene}acetate.

EXAMPLE 2

To a solution of 3.0 g of 4-bromo-2-methylbenzoic acid in 20 ml of THF and 1 drop of DMF, 1.9 ml of oxalyl chloride was added under ice cooling, and the mixture was stirred at room temperature for 2 hours. The reaction solution was concentrated, and the residue was mixed with 3 ml of toluene and concentrated again. The obtained residue was mixed with 20 ml of pyridine and 3.5 g of methyl (2Z)-(4,4-difluoro-1,2,3,4-tetrahydro-5H-1-benzazepin-5-ylidene)acetate and the mixture was stirred at room temperature for 12 hours. The reaction mixture was concentrated, then to the mixture was added chloroform and 1M aqueous NaOH and was extracted. The organic layer was washed with water and brine, and dried over anhydrous sodium sulfate. After evaporation of the solvent, the residue was purified by silica gel column chromatography (hexane-EtOAc (6:1)) to obtain 5.94 g of methyl (2Z)-[1-(4-bromo-2-methylbenzoyl)-4,4-difluoro-1,2,3,4-tetrahydro-5H-1-benzazepin-5-ylidene]acetate.

EXAMPLE 3

To a solution of 4.62 g of 2-(trifluoromethyl)benzoic acid in 30 ml of sulfuric acid, 3.48 g of 1,3-dibromo-5,5-dimethylhydantoin were added. The mixture was stirred at room temperature for 15 hours, and then added to ice water dropwise. 5M NaOH aq. were added to the reaction solution to control pH of the solution to 12, and then the reaction solution was extracted with chloroform. To the aqueous layer, concentrated hydrochloric acid was added to control the pH of the solution to 1, and then the reaction solution was extracted with chloroform. The organic layer was washed with water and brine, and dried over anhydrous sodium sulfate. After evaporation of the solvent, 20 ml of THF and 1 drop of DMF were added to the residue, and 2.5 ml of oxalyl chloride were added thereto under ice cooling, and then the mixture was stirred at room temperature for 2 hours. The reaction solution was concentrated under reduced pressure, and the residue was mixed with 10 ml of toluene and concentrated again. To the obtained residue, 20 ml of pyridine and 6.2 g of methyl (2Z)-(4,4-difluoro-1,2,3,4-tetrahydro-5H-1-benzazepin-5-ylidene)acetate were added, and the mixture was stirred at room temperature for 12 hours. The reaction solution was concentrated, and the residue was mixed with chloroform and 1M HCl aq. and extracted. The organic layer was washed with water and brine, and dried over anhydrous sodium sulfate. After evaporation of the solvent, the residue was purified by silica gel column chromatography (hexane-EtOAc(6:1)). And, the residue obtained by concentration under reduced pressure was crystallized from EtOH to obtain 3.66 g of methyl (2Z)-{1-[4-bromo-2-(trifluoromethyl)benzoyl]-4,4-difluoro-1,2,3,4-tetrahydro-5H-1-benzazepin-5-ylidene}acetate.

EXAMPLE 4

To a solution of 2.0 g of the compound of Example 2 in 30 ml of toluene, 22.35 g of tert-butyl hydrazine carboxylate, 1.43 g of cesium carbonate, 400 mg of tris(dibenzylideneacetone)dipalladium (0), and 740 mg of 1,1'-bis(diphenylphosphine)ferrocene were added, and the mixture was stirred at 100° C. for 4 hours. After cooling the reaction solution, insoluble matter was filtered, and EtOAc and 10% citric acid aqueous solution were added to the filtrate to extract it. The organic layer was washed with water and brine, and dried over anhydrous sodium sulfate anhydride. After evaporation of the solvent, the residue was purified by silica gel column chromatography (hexane-EtOAc (2:1)) to obtain 1.0 g of tert-butyl 1-(4-{[(5Z)-4,4-difluoro-5-(2-methyl-2-oxoethylidene)-2,3,4,5-tetrahydro-1H-1-benzazepin-1-yl]carbonyl}-3-methylphenyl)hydrazine carboxylate.

EXAMPLE 5

To a solution of 1.0 g of the compound of Example 4 in 10 ml of EtOAc, 10 ml of 4M HCl-EtOAc were added, and the mixture was stirred at room temperature for 4 hours. The reaction solution was concentrated under reduced pressure, and the residue was mixed with saturated NaHCO$_3$ aq. and chloroform and extracted. The organic layer was washed with water and brine, and dried over anhydrous sodium sulfate. After evaporation of the solvent, 40 ml of MeOH and 275 mg of acetylacetaldehyde dimethylacetal were added to the residue, and the mixture was heated under reflux for 1.5 hours. To the reaction solution, 3 drops of conc. hydrochloric acid were added, and the mixture was heated under reflux for 30 minutes again. The reaction solution was cooled, and then concentrated under reduced pressure. The residue was mixed with saturated sodium hydrogen carbonate aqueous solution and chloroform and extracted. The organic layer was washed with water and brine, and dried over anhydrous sodium sulfate. After evaporation of the solvent, the residue was purified by silica gel column chromatography (hexane-EtOAc (4:1)) to obtain 561 mg of methyl (2Z)-{4,4-difluoro-1-[2-methyl-4-(3-methyl-1H-pyrazol-1-yl)benzoyl]-1,2,3,4-tetrahydro-5H-1-benzazepin-5-ylidene}acetate.

EXAMPLE 6

38.0 g of the compound of Example 1 were dissolved in 120 ml of MeOH and 120 ml of THF, 100 ml of 1M NaOH aq. was added at room temperature, and the mixture was stirred for 10 hours. Approximately 200 ml of the solvent were evaporated under reduced pressure, 0.5M HCl aq. were added to the residue under ice cooling, and the mixture was stirred for 1 hour. Thus formed white precipitations were filtered and dried to obtain 36.5 g of (2Z)-{1-[2-chloro-4-(3-methyl-1H-pyrazol-1-yl)benzoyl]-4,4-difluoro-1,2,3,4-tetrahydro-1H-1-benzazepin-5-ylidene}acetic acid in the form of powder.

EXAMPLE 7

To a solution of 229 mg of the compound of Example 6, 71 mg of HOBt and 101 mg of EDCI.HCl in 3 ml of DMF, 35 mg of thiophen-2-ylmethylamine were added, and the mixture was stirred at room temperature overnight. The reaction solution was mixed with saturated sodium bicarbonate aqueous solution and chloroform, and extracted. The organic layer was dried over anhydrous magnesium sulfate, and the solvent was evaporated. Then, the residue was purified by silica gel column chromatography (chloroform-MeOH (30:1)). The residue obtained by concentration under reduced pressure was crystallized from a 2-propanol-diisopropyl ether solvent mixture to obtain 61 mg of (2Z)-2-{1-[2-chloro-4-(3-methyl-1H-pyrazol-1-yl]benzoyl}-4,4-difluoro-1,2,3,4, -tetrahydro-5H-1-benzazepin-5-ylidene}-N-(thiophen-2-ylmethyl)acetamide.

EXAMPLE 8

210 mg of the compound of Example 6 were dissolved in 20 ml of dichloroethane, 2 ml of thionyl chloride were added, and the mixture was stirred at room temperature for 30 minutes. The reaction solution was concentrated under reduced pressure, and the residue was mixed with toluene and concentrated again. The obtained acid chloride form were dissolved in 30 ml of acetonitrile, and added dropwise to 30 ml of ammonia water at room temperature. After stirring at room temperature for 12 hours, the formed white precipitations were filtered and dried to obtain 259 mg of (2Z)-2-{1-[2-chloro-4-(3-methyl-1H-pyrazol-1-yl)benzoyl]-4,4-difluoro-1,2,3,4-tetrahydro-5H-benzazepine}acetamide in the form of powder.

EXAMPLE 9

915 mg of the compound of Example 14 were dissolved in 20 ml of MeOH, 3 ml of 1M NaOH aq. were added, and the mixture was stirred at room temperature for 15.5 hours. The solvent was evaporated under reduced pressure, and then the residue was acidified with 1M HCl aq. and extracted with chloroform. The organic layer was washed with water and brine, and dried over anhydrous sodium sulfate. After evaporation of the solvent, the obtained carboxylic acid intermediate was dissolved in 10 ml of DMF, 0.24 ml of 2-picolyl amine, 0.39 g of HOBt and 0.61 g of EDCI.HCl were added thereto, and the mixture was stirred at room temperature for 84 hours. The reaction solution was mixed with water and EtOAc, and extracted. The organic layer was washed with brine, and dried over anhydrous sodium sulfate. After evaporation of the solvent, the residue was purified by silica gel column chromatography (chloroform-MeOH (35:1)). The residue obtained by concentration under reduced pressure was dissolved in EtOAc, 0.4 ml of 4M HCl-EtOAc solution was added thereto, and the solvent was evaporated under reduced pressure. The obtained residue was crystallized from EtOH to obtain 0.456 g of (2Z)-2-[1-(2-chloro-4-pyrrolidin-1-ylbenzoyl)-4,4-difluoro-1,2,3,4-tetrahydro-5H-1-benzazepin-5-ylidene]-N-(pyridin-2-ylmethyl)acetamide hydrochloride.

EXAMPLE 10

0.25 g of the compound of Example 93 were dissolved in 10 ml of MeOH, 10 ml of 1M NaOH were added, and the mixture was stirred at room temperature for 16 hours. The reaction solution was neutralized with 1M HCl aq., and extracted with chloroform. The organic layer was washed with water and brine, and dried over anhydrous magnesium sulfate. After evaporation of the solvent, the residue was crystallized from an EtOAc-hexane solvent mixture to obtain 116 mg of [((2Z)-2-{1-[2-chloro-4-(3-methyl-1H-pyrazol-1-yl)benzoyl]-4,4-difluoro-1,2,3,4-tetrahydro-5H-1-benzazepin-5-ylidene}acetyl)amino]acetic acid.

EXAMPLE 11

To a solution of 258 mg of the compound of Example 10, 71 mg of HOBt and 101 mg of EDCI.HCl in 5 ml of THF, and 0.5 ml of 2.0 M methylamine-THF solution were added, and the mixture was stirred at room temperature overnight. The reaction solution was mixed with saturated NaHCO₃ aq. and extracted with chloroform. The organic layer was dried over anhydrous magnesium sulfate. The crude product obtained by evaporation of the solvent was purified by silica gel column chromatography (chloroform-MeOH (30:1)). The residue obtained by concentration under reduced pressure was crystallized from a 2-propanol-hexane solvent mixture to obtain 51 mg of (2Z)-2-{1-[2-chloro-4-(3-methyl-1H-pyrazol-1-yl)benzoyl]-4,4-difluoro-1,2,3,4-tetrahydro-5H-1-benzazepin-5-ylidene}-N-[2-(methylamino)-2-oxoethyl]acetamide.

EXAMPLE 12

To a solution of 265 mg of the compound of Reference Example 90 in 5 ml of THF, 82 mg of 1,1'-carbonylbis-1H-imidazole were added, and the mixture was stirred at room temperature for 0.1 hour. Then, ammonia water was added to the reaction solution, and the mixture was stirred at room temperature for 22 hours. The reaction solution was mixed with water and EtOAc, and extracted therewith. The organic layer was washed with water and brine, and dried over anhydrous magnesium sulfate. The crude product obtained by evaporation of the solvent was purified by silica gel column chromatography (chloroform-MeOH(100:1)). The residue obtained by concentration under reduced pressure was crystallized from a 2-propanol-diisopropyl ether solvent mixture to obtain 41 mg of (2Z)-N-[2-amino-2-oxoethyl]-N-methyl-2-{1-[2-chloro-4-(3-methyl-1H-pyrazol-1-yl)benzoyl]-4,4-difluoro-1,2,3,4-tetrahydro-5H-1-benzazepin-5-ylidene}acetamide.

EXAMPLE 13

To a solution of 0.35 g of the compound of Reference Example 85 in 10 ml of THF and 1 drop of DMF, 0.22 ml of thionylchloride were added under ice cooling, and the mixture was stirred at room temperature for 2.5 hours. The reaction solution was concentrated under reduced pressure, and the residue was mixed with 3 ml of toluene and concentrated again. The obtained residue was dissolved in 20 ml of acetonitrile, 0.4 g of the compound of Reference Example 89 and 0.4 ml of pyridine were added, and the mixture was stirred at 80° C. for 17 hours. After cooling the reaction solution, the solvent was evaporated, and the residue was mixed with chloroform and 10% citric acid aqueous solution, and extracted therewith. The organic layer was washed with saturated sodium bicarbonate aqueous solution, water, and brine, and the dried over anhydrous sodium sulfate. After evaporation of the solvent, the residue was purified by silica gel column chromatography (chloroform-MeOH-ammonia water (25:0:0.1)). The residue obtained by concentration under reduced pressure was dissolved in EtOAc, 0.18 ml of 4M HCl-EtOAc solution was added thereto, and the solvent was evaporated under reduced pressure. The obtained residue was crystallized from EtOH to obtain 0.176 g of (2Z)-2-[1-(2-chloro-4-piperidin-1-yl-benzoyl)-4,4-difluoro-1,2,3,4-tetrahydro-5H-1-benzazepin-5-ylidene]-N-(pyridine-2-ylmethyl) acetamide hydrochloride.

The structures and physicochemical data of the compounds of Examples are shown in Tables 9. Additionally, the structures and physicochemical data of the compounds obtained by the same production method are also shown in Tables 9 to 16. The symbols in the Tables have the following meanings.

Ex: Number of Example

Salt: salt (HCl: hydrochloride, inorganic material: free form)

Syn: synthesis method (The number indicates the number of Example of which method is applied)

$R^A$, $R^B$, $R^C$, $R^D$, $R^{1-4}$: substituent group in the general formula (nPen: normal pentyl, cHex: cyclohexyl, Ac: acetyl, Ms: mesyl, Boc: tert-butyloxycarbony, py: pyridyl, fur:furyl, thia: thiazolyl, bthia: benzothiazolyl. Thus, as examples, —NH$_2$CH$_2$-(2-py) indicates pyridine-2-ylmethylamino, —NH$_2$CH$_2$—(4-HO-3-MeO-Ph) indicates 4-hydroxy-3-methoxybenzylamino, and 2-HOCH$_2$-1-pipe indicates 2-hydroxymethylpiperidin-1-yl.)

TABLE 9

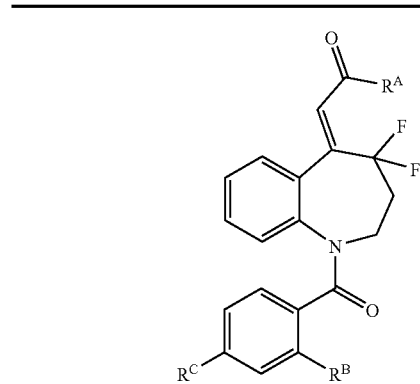

| Ex(Salt) | $R^A$ | $R^B$ | $R^C$ | MS | Syn |
|---|---|---|---|---|---|
| 1 | —OMe | Cl | 3-Me-1-pra | 472. | 1 |
| 2 | —OMe | Me | —Br | 452. | 2 |
| 3 | —OMe | CF$_3$ | —Br | 504. | 3 |
| 4 | —OMe | Me | —N(Boc)NH$_2$ | 502. | 4 |
| 5 | —OMe | Me | 3-Me-1-pra | 452. | 5 |
| 6 | —OH | Cl | 3-Me-1-pra | 458. | 6 |
| 7 | —NHCH$_2$-(2-the) | Cl | 3-Me-1-pra | 553. | 7 |
| 8 | —NH$_2$ | Cl | 3-Me-1-pra | 457. | 8 |
| 9(HCl) | —NHCH$_2$-(2-py) | Cl | 1-pyrr | 538. | 9 |
| 10 | —NHCH$_2$CO$_2$H | Cl | 3-Me-1-pra | 515. | 10 |
| 11 | —NHCH$_2$CONHMe | Cl | 3-Me-1-pra | 528. | 11 |
| 12 | —N(Me)CH$_2$CONH$_2$ | Cl | 3-Me-1-pra | 528. | 12 |
| 13(HCl) | —NHCH$_2$-(2-py) | Cl | 1-pipe | 551. | 13 |

TABLE 10

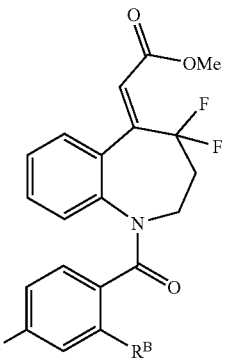

| Ex(Salt) | $R^B$ | $R^C$ | MS | Syn |
|---|---|---|---|---|
| 14 | Cl | 1-pyrr | 461. | 1 |
| 15 | Cl | 2-Me-1-pyrr | 475. | 1 |
| 16 | Cl | 3-Me-1-pyrr | 475. | 1 |
| 17 | Cl | 3-(R)—Me-1-pyrr | MM;474. | 1 |
| 18 | Cl | 3-(S)—Me-1-pyrr | 475. | 1 |
| 19 | Cl | 3,3-diMe-1-pyrr | 489. | 1 |
| 20 | Cl | 3-Me-3-Et-1-pyrr | 503. | 1 |
| 21 | Cl | 3-F-1-pyrr | 479. | 1 |
| 22 | Cl | 3-Ph-1-pyrr | 538. | 1 |
| 23 | CF$_3$ | 1-pyrr | 495. | 1 |
| 24 | CF$_3$ | 3-(R)—Me-1-pyrr | 509. | 1 |
| 25 | CF$_3$ | 3-(S)—Me-1-pyrr | 509. | 1 |
| 26 | CF$_3$ | 3,4-diMe-1-pyrr | 523. | 1 |
| 27 | CF$_3$ | 3,3-diMe-pyrr | 523. | 1 |
| 28 | Me | 1-pyrr | 441. | 1 |
| 29 | Cl | 1-pra | 458. | 1 |
| 30 | Cl | 5-Me-1-pra | 472. | 1 |
| 31 | Cl | 3-Et-1-pra | 486. | 1 |
| 32 | Cl | 3-iPr-1-pra | 500. | 1 |
| 33 | Cl | 3-cPr-1-pra | 498. | 1 |
| 34 | Cl | 3,5-diMe-1-pra | 486. | 1 |
| 35 | Cl | 4-Br-1-pra | 536,538. | 1 |
| 36 | Cl | 3-Ph-1-pra | 534. | 1 |
| 37 | Cl | 3-(2-the)-1-pra | 540. | 1 |
| 38 | CF$_3$ | 3-Me-1-pra | 506. | 1 |
| 39 | CF$_3$ | 3-Me-1-pra | 506. | 5 |
| 40 | CF$_3$ | 4-Me-1-pra | 506. | 1 |
| 41 | CF$_3$ | 5-Me-1-pra | 506. | 1 |
| 42 | CF$_3$ | 3-iPr-1-pra | 534. | 1 |
| 43 | CF$_3$ | 3-F$_3$C-1-pra | 560. | 1 |
| 44 | CF$_3$ | 3-tBu-1-pra | 548. | 1 |
| 45 | CF$_3$ | 3,5-diMe-1-pra | 520. | 1 |
| 46 | Cl | 3-Me-1-pipe | 565. | 1 |
| 47 | Cl | 3,5-diMe-1-pipe | 579. | 1 |
| 48 | Cl | 4-mor | 477. | 1 |
| 49 | Cl | pyrrol-1-yl | 457. | 1 |
| 50 | Cl | 2,5-diMe-pyrrol-1-yl | 485. | 1 |
| 51 | CF$_3$ | 2,5-dihydro-1H-pyrrol-1-yl | 493. | 1 |
| 52 | Cl | 2-Me-imidazol-1-yl | 472. | 1 |
| 53 | Cl | 1-bimid | 508. | 1 |
| 54 | Cl | indazol-1-yl | 508. | 1 |
| 55 | CF$_3$ | —N(Boc)NH$_2$ | 556. | 4 |

TABLE 11

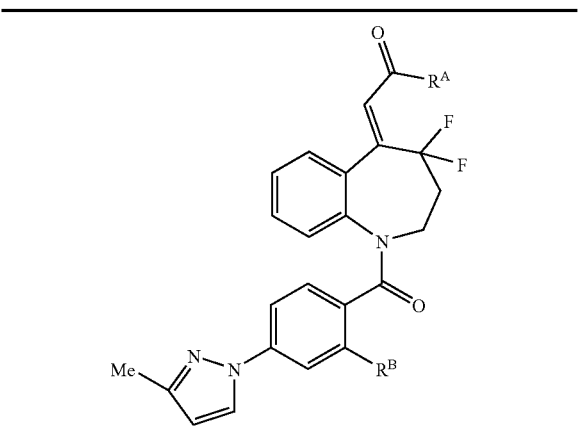

| Ex (Salt) | R^A | R^B | MS | Syn |
|---|---|---|---|---|
| 56 | 3-HO-1-pyrr | Cl | 527. | 7 |
| 57 | 3-HO-1-pipe | Cl | 541. | 7 |
| 58 | 3-H$_2$NOC-1-pipe | Cl | 568. | 7 |
| 59 | 4-H$_2$NOC-1-pipe | Cl | 568. | 7 |
| 60 | 2-HOCH$_2$-1-pipe | Cl | 555. | 7 |
| 61 | 3-HOCH$_2$-1-pipe | Cl | 555. | 7 |
| 62 | —NH-(2-HO-cHex) | Cl | 555. | 7 |
| 63 | —NHPh | Cl | 533. | 7 |
| 64 | —NH-(2-HO—Ph) | Cl | 549. | 7 |
| 65 | —NH-(3-HO—Ph) | Cl | 549. | 7 |
| 66 | —NH-(4-HO—Ph) | Cl | 549. | 7 |
| 67 | —NH-(3-Ac—Ph) | Cl | 575. | 7 |
| 68 | —NH-(3-HO$_2$C—Ph) | Cl | 577. | 7 |
| 69 | —NH-(3-MeO$_2$C—Ph) | Cl | 591. | 7 |
| 70 | —NH-(2-H$_2$NOC—Ph) | Cl | 576. | 7 |
| 71 | —NH-(3-H$_2$NOC—Ph) | Cl | 576. | 7 |
| 72 | —NH-(4-H$_2$NOC—Ph) | Cl | 576. | 7 |
| 73 | —NH-(3-MeNHCO—Ph) | Cl | 590. | 7 |
| 74 | —NH-(3-Me—Ph) | Cl | 547. | 7 |
| 75 | —NH-(2-HOCH$_2$—Ph) | Cl | 563. | 7 |
| 76 | —NH-(3-HOCH$_2$—Ph) | Cl | 563. | 7 |
| 77 | —NH-(4-HOCH$_2$—Ph) | Cl | 563. | 7 |
| 78 | —NH-(3-HO(CH$_2$)$_2$—Ph) | Cl | 577. | 7 |
| 79 | —NH-(3-MeCH(OH)—Ph) | Cl | 577. | 7 |
| 80 | —NH-(2-HOCH$_2$CH(OH)—Ph) | Cl | 593. | 7 |
| 81 | —NH-(4-HOCH$_2$CH(OH)—Ph) | Cl | 593. | 7 |
| 82 | —NH-(3-MeOCH$_2$—Ph) | Cl | 577. | 7 |
| 83 | —NH-(3-H$_2$NOCCH$_2$—Ph) | Cl | 590. | 7 |
| 84 | —NH-(3-H$_2$NOC(CH$_2$)$_2$—Ph) | Cl | 604. | 7 |
| 85 | —NH-(3-H$_2$NOC—(E)—CH=CH—Ph) | Cl | 602. | 7 |
| 86 | —NH-(3-F—Ph) | Cl | 551. | 7 |
| 87 | —NH-(3-Ms—Ph) | Cl | 611. | 7 |
| 88 | —NH-(3-AcNH—Ph) | Cl | 590. | 7 |
| 89 | —NH-(3-the) | Cl | 539. | 7 |
| 90 | (3-pyrrolidinone-NH-) | Cl | 540. | 7 |
| 91 | (3-tetrahydrofuranone-NH-) | Cl | 541. | 7 |
| 92 | (3-thiolanone-NH-) | Cl | 557. | 7 |
| 93 | —NHCH$_2$CO$_2$Me | Cl | 529. | 7 |
| 94 | —NHCH$_2$CONH$_2$ | Cl | 514. | 7 |
| 95 | —NHCH$_2$Ph | Cl | 547. | 7 |
| 96 | —NHCH$_2$-(4-HO—Ph) | Cl | 563. | 7 |
| 97 | —NHCH$_2$-(3-HO—Ph) | Cl | 563. | 7 |
| 98 | —NHCH$_2$-(2-HO—Ph) | Cl | 563. | 7 |
| 99 | —NHCH$_2$-(3,4-diHO—Ph) | Cl | 579. | 7 |
| 100 | —NHCH$_2$-(4-MeO—Ph) | Cl | 577. | 7 |
| 101 | —NHCH$_2$-(3,4-diMeO—Ph) | Cl | 607. | 7 |
| 102 | —NHCH$_2$-(4-HO-3-MeO—Ph) | Cl | 593. | 7 |
| 103 | —NHCH$_2$-(4-HO$_2$C—Ph) | Cl | 591. | 7 |
| 104 | —NHCH$_2$-(4-MeO$_2$C—Ph) | Cl | 605. | 7 |
| 105 | —NHCH$_2$-(4-H$_2$NOC—Ph) | Cl | 590. | 7 |
| 106 | —NHCH$_2$-(3-H$_2$NOC—Ph) | Cl | 590. | 7 |
| 107 | —NHCH$_2$-(3-HOCH$_2$—Ph) | Cl | 577. | 7 |
| 108 | —NHCH$_2$-(4-F—Ph) | Cl | 565. | 7 |
| 109 | —NHCH$_2$-(4-H$_2$NO$_2$S—Ph) | Cl | 626. | 7 |
| 110 (HCl) | —NHCH$_2$-(2-py) | Cl | 548. | 7 |
| 111 | —NHCH$_2$-(6-HO-2-py) | Cl | 564. | 7 |
| 112 | —NHCH$_2$-(5-MeO-2-py) | Cl | 578. | 7 |
| 113 (HCl) | —NHCH$_2$-(6-MeO-2-py) | Cl | 578. | 7 |
| 114 | —NHCH$_2$-(6-iPrO-2-py) | Cl | 606. | 7 |
| 115 | —NHCH$_2$-(6-H$_2$NOC-2-py) | Cl | 591. | 7 |
| 116 | —NHCH$_2$-(6-Me$_2$NOC-2-py) | Cl | 619. | 7 |
| 117 | —NHCH$_2$-(6-cyano-2-py) | Cl | 573. | 7 |
| 118 | —NHCH$_2$-(5-Me-2-py) | Cl | 562. | 7 |
| 119 (HCl) | —NHCH$_2$-(6-Me-2-py) | Cl | 562. | 7 |
| 120 (HCl) | —NHCH$_2$-(6-HOCH$_2$-2-py) | Cl | 578. | 7 |
| 121 (HCl) | —NHCH$_2$-(6-H$_2$N-2-Me-3-py) | Cl | 577. | 7 |
| 122 (HCl) | —NHCH$_2$-(6-H$_2$N-2-py) | Cl | 563. | 7 |
| 123 | —NHCH$_2$-(6-Me$_2$N-2-py) | Cl | 591. | 7 |
| 124 | —NHCH$_2$-(6-F-2-py) | Cl | 566. | 7 |
| 125 | —NHCH$_2$-(6-Cl-2-py) | Cl | 582. | 7 |
| 126 (HCl) | —NHCH$_2$-(3-py) | Cl | 548. | 7 |
| 127 | —NHCH$_2$-(3-the) | Cl | 553. | 7 |
| 128 | —NHCH$_2$-(2-fur) | Cl | 537. | 7 |
| 129 | —NHCH$_2$-(2-thia) | Cl | 554. | 7 |
| 130 | —NHCH$_2$-(4-thia) | Cl | 554. | 7 |
| 131 (HCl) | —NHCH$_2$-(pyrazol-2-yl) | Cl | 549. | 7 |
| 132 | —NHCH$_2$-(pyridazin-3-yl) | Cl | 549. | 7 |
| 133 | —NHCH$_2$-(pyrimidin-4-yl) | Cl | 549. | 7 |
| 134 | —NHCH$_2$-(pyridazin-4-yl) | Cl | 549. | 7 |
| 135 (HCl) | —NHCH$_2$-(2-bimid) | Cl | 587. | 7 |
| 136 (HCl) | —NHCH$_2$-(1-Me-2-bimid) | Cl | 601. | 7 |
| 137 | —NHCH$_2$-(2-bthia) | Cl | 604. | 7 |

TABLE 11-continued

| Ex (Salt) | R^A | R^B | MS | Syn |
|---|---|---|---|---|
| 138 | —NHCH(CONH₂)₂ | Cl | 557. | 7 |
| 139 | —NH(CH₂)₂OH | Cl | 501. | 7 |
| 140 | —(R)—NHCH(Me)CH₂OH | Cl | 515. | 7 |
| 141 | —(S)—NHCH(Me)CH₂OH | Cl | 515. | 7 |
| 142 | —(R)—NHCH₂CH(Me)OH | Cl | 515. | 7 |
| 143 | —(S)—NHCH₂CH(Me)OH | Cl | 515. | 7 |
| 144 | —NHC(Me)₂CH₂OH | Cl | 529. | 7 |
| 145 | —NHCH₂C(Me)₂OH | Cl | 529. | 7 |
| 146 | —NH(CH₂)₂OMe | Cl | 515. | 7 |
| 147 | —NH(CH₂)₂CONH₂ | Cl | 528. | 7 |
| 148 | —NHCH(CO₂Me)CH₂OH | Cl | 559. | 7 |
| 149 | —NHCH(CONH₂)CH₂OH | Cl | 544. | 7 |
| 150 | —NHCH(Ph)CH₂OH | Cl | 577. | 7 |
| 151 | —NH(CH₂)₃OH | Cl | 515. | 7 |
| 152 | —NHCH₂CH(OH)CH₂OH | Cl | 531. | 7 |
| 153 | —NHCH(CH₂OH)₂ | Cl | 531. | 7 |
| 154 | —NH(CH₂)₄OH | Cl | 529. | 7 |
| 155 | —NHnPen | Cl | 527. | 7 |
| 156 | —NMe₂ | Cl | 485. | 7 |
| 157 | —N(Me)(CH₂)₂OH | Cl | 515. | 7 |
| 158 | —N((CH₂)₂OH)₂ | Cl | 545. | 7 |
| 159 | —N(CH₂CONH₂)((CH₂)₂OH) | Cl | 558. | 7 |
| 160 | —N(CH₂-2-py)((CH₂)₂OH) | Cl | 592. | 7 |
| 161 | —N(CH₂CONH₂)₂ | Cl | 571. | 7 |
| 162 | —NH₂ | CF₃ | 491. | 9(8) |
| 163 | —NH(CH₂)₂OH | CF₃ | 535. | 9 |
| 164 | —NHCH₂CONH₂ | CF₃ | 548. | 9 |
| 165 (HCl) | —NHCH₂-(2-py) | CF₃ | 582. | 9 |
| 166 | —NHCH₂CONH₂ | Me | 494. | 9 |
| 167 | —NH₂ | Me | 437. | 9(8) |

TABLE 12

| Ex(Salt) | R^B | R^C | MS | Syn |
|---|---|---|---|---|
| 168 | Cl | 1-pyrr | 446. | 9(8) |
| 169 | Cl | 3,3-diMe-1-pyrr | 474. | 9(8) |
| 170 | Cl | 3-F-1-pyrr | 464. | 9(8) |
| 171 | Cl | 3-Ph-1-pyrr | 522. | 9(8) |
| 172 | Cl | 3-Me-3-Et-1-pyrr | 488. | 9(8) |
| 173 | Cl | 3-(S)—Me-1-pyrr | 460. | 9(8) |
| 174 | Cl | 3-(R)—Me-1-pyrr | 460. | 9(8) |
| 175 | CF₃ | 1-pyrr | 480. | 9(8) |
| 176 | CF₃ | 3-(R)—Me-1-pyrr | 494. | 9(8) |
| 177 | CF₃ | 3-(S)—Me-1-pyrr | 494. | 9(8) |
| 178 | CF₃ | 3,3-diMe-1-pyrr | 508. | 9(8) |
| 179 | CF₃ | 3,4-diMe-1-pyrr | 508. | 9(8) |
| 180 | CF₃ | 4-Me-1-pra | 491. | 9(8) |
| 181 | CF₃ | 5-Me-1-pra | 491. | 9(8) |
| 182 | CF₃ | 3-iPr-1-pra | 519. | 9(8) |
| 183 | CF₃ | 3-tBu-1-pra | 533. | 9(8) |
| 184 | CF₃ | 3-F₃C-1-pra | 545. | 9(8) |
| 185 | CF₃ | 3,5-diMe-1-pra | 505. | 9(8) |

TABLE 13

| Ex(Salt) | R^B | R^C | MS | Syn |
|---|---|---|---|---|
| 186(HCl) | Cl | 2-Me-1-pyrr | 551. | 9 |
| 187(HCl) | Cl | 3-Me-1-pyrr | 551. | 9 |
| 188(HCl) | Cl | 3,3-diMe-1-pyrr | 565. | 9 |
| 189(HCl) | Cl | 3-F-1-pyrr | 555. | 9 |
| 190(HCl) | Cl | 1-pra | 534. | 9 |
| 191(HCl) | Cl | 5-Me-1-pra | 547. | 9 |
| 192(HCl) | Cl | 3-Et-1-pra | 562. | 9 |
| 193(HCl) | Cl | 3-iPr-1-pra | 576. | 9 |
| 194(HCl) | Cl | 3-cPr-1-pra | 574. | 9 |
| 195(HCl) | Cl | 3,5-diMe-1-pra | 562. | 9 |
| 196 | Cl | 4-Br-1-pra | 612,614. | 9 |
| 197 | Cl | 3-Ph-1-pra | 610. | 9 |
| 198 | Cl | 3-(2-the)-1-pra | 616. | 9 |
| 199(HCl) | Cl | 3-Me-1-pipe | 565. | 9 |
| 200(HCl) | Cl | 3,5-diMe-1-pipe | 579. | 9 |
| 201(HCl) | Cl | 4-mor | 553. | 9 |

TABLE 13-continued

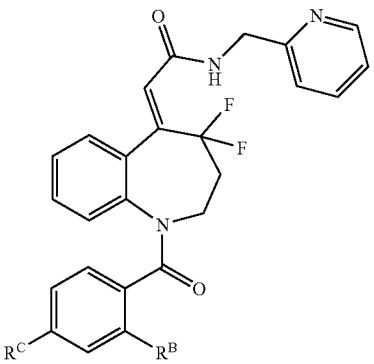

| Ex(Salt) | R$^B$ | R$^C$ | MS | Syn |
|---|---|---|---|---|
| 202(HCl) | Cl | azepin-1-yl | 565. | 13 |
| 203(HCl) | Cl | pyrrol-1-yl | 533. | 9 |
| 204(HCl) | Cl | 2,5-diMe-pyrrol-1-yl | 561. | 9 |
| 205 | Cl | 2-Me-1-imid | 548. | 9 |
| 206(HCl) | Cl | 1-bimid | 584. | 9 |
| 207(HCl) | Cl | indazol-1-yl | 584. | 9 |
| 208(HCl) | CF$_3$ | 1-pyrr | 571. | 9 |
| 209(HCl) | Me | 1-pyrr | 517. | 9 |

TABLE 14

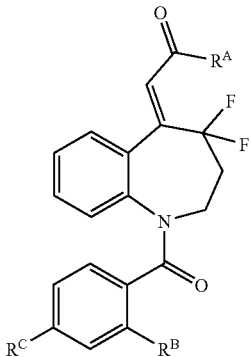

| Ex (Salt) | R$^A$ | R$^B$ | R$^C$ | MS | Syn |
|---|---|---|---|---|---|
| 210 | —NH(CH$_2$)$_2$OH | Cl | 1-pyrr | 490. | 9 |
| 211 | —NH(CH$_2$)$_2$OH | Cl | 3-(R)—Me-1-pyrr | 504. | 9 |
| 212 | —NH(CH$_2$)$_2$OH | Cl | 3-(S)—Me-1-pyrr | 504. | 9 |
| 213 | —NH(CH$_2$)$_2$OH | Cl | 3,3-diMe-1-pyrr | 518. | 9 |
| 214 | —NH(CH$_2$)$_2$OH | CF$_3$ | 1-pyrr | 524. | 9 |
| 215 | —NH(CH$_2$)$_2$OH | CF$_3$ | 3-(R)—Me-1-pyrr | 538. | 9 |
| 216 | —NH(CH$_2$)$_2$OH | CF$_3$ | 3-(S)—Me-1-pyrr | 538. | 9 |
| 217 | —NH(CH$_2$)$_2$OH | CF$_3$ | 3,3-diMe-1-pyrr | 552. | 9 |
| 218 | —NH(CH$_2$)$_2$OH | CF$_3$ | 3,4-diMe-1-pyrr | 552. | 9 |
| 219 | —NH(CH$_2$)$_2$OH | CF$_3$ | 4-Me-1-pra | 535. | 9 |
| 220 | —NHCH$_2$CONH$_2$ | Cl | 1-pyrr | 503. | 9 |
| 221 | —NHCH$_2$CONH$_2$ | Cl | 3-(R)—Me-1-pyrr | 517. | 9 |
| 222 | —NHCH$_2$CONH$_2$ | Cl | 3-(S)—Me-1-pyrr | 517. | 9 |

TABLE 14-continued

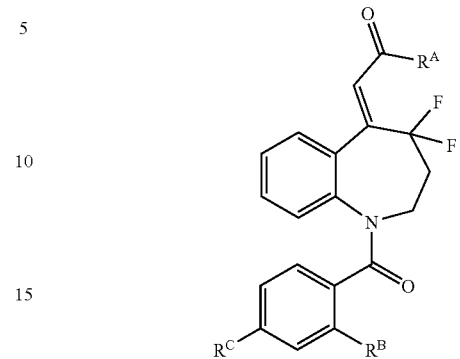

| Ex (Salt) | R$^A$ | R$^B$ | R$^C$ | MS | Syn |
|---|---|---|---|---|---|
| 223 | —NHCH$_2$CONH$_2$ | Cl | 3,3-diMe-1-pyrr | 531. | 9 |
| 224 | —NHCH$_2$CONH$_2$ | Cl | 3-Ph-1-pyrr | 579. | 9 |
| 225 | —NHCH$_2$CONH$_2$ | Cl | 3-Me-3-Et-1-pyrr | 545. | 9 |
| 226 | —NHCH$_2$CONH$_2$ | CF$_3$ | 1-pyrr | 537. | 9 |
| 227 | —NHCH$_2$CONH$_2$ | CF$_3$ | 3-(R)—Me-1-pyrr | 551. | 9 |
| 228 | —NHCH$_2$CONH$_2$ | CF$_3$ | 3-(S)—Me-1-pyrr | 551. | 9 |
| 229 | —NHCH$_2$CONH$_2$ | CF$_3$ | 3,3-diMe-1-pyrr | 565. | 9 |
| 230 | —NHCH$_2$CONH$_2$ | CF$_3$ | 3,4-diMe-1-pyrr | 565. | 9 |
| 231 | —NHCH$_2$CONH$_2$ | CF$_3$ | 3-F$_3$C-1-pra | 602. | 9 |
| 232 | —NHCH$_2$CONH$_2$ | CF$_3$ | 4-Me-1-pra | 548. | 9 |
| 233 | —NHCH$_2$CONH$_2$ | CF$_3$ | 3-tBu-1-pra | 590. | 9 |
| 234 | —NHCH$_2$CONH$_2$ | CF$_3$ | 2,5-dihydropyrrol-1-yl | 535. | 9 |

TABLE 15

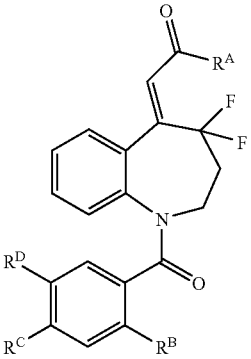

| Ex(Salt) | R$^A$ | R$^B$ | R$^C$ | R$^D$ | MS | Syn |
|---|---|---|---|---|---|---|
| 235 | OMe | Cl | H | 1-pyrr | 461. | 1 |
| 236 | OMe | Cl | 3-Me-1-pra | F | 490. | 1 |
| 237(HCl) | —NHCH$_2$-(2-py) | Cl | H | 1-pyrr | 537. | 9 |
| 238 | —NH$_2$ | Cl | 3-Me-1-pra | F | 474. | 9(8) |

TABLE 16

| Ex(Salt) | R^IA | R^B | R^C | MS | Syn |
|---|---|---|---|---|---|
| 239 | —NMe₂ | Cl | 3-Me-1-pra | 542. | 11 |
| 240 | —NH(CH₂)₂OH | Cl | 3-Me-1-pra | 558. | 11 |
| 241 | 1-pyrr | Cl | 3-Me-1-pra | 568. | 11 |

TABLE 16-continued

| Ex(Salt) | R^IA | R^B | R^C | MS | Syn |
|---|---|---|---|---|---|
| 242 | 1-pipe | Cl | 3-Me-1-pra | 582. | 11 |
| 243 | 2-HOCH₂-1-pipe | Cl | 3-Me-1-pra | 612. | 11 |
| 244 | 3-HOCH₂-1-pipe | Cl | 3-Me-1-pra | 612. | 11 |

NMR data of the compounds of some Examples are shown in Table 17. The term 'NMR' indicates δ(ppm) of the peaks in $^1$H-NMR employing DMSO-$d_6$ as a measuring solvent unless otherwise indicated, using $(CH_3)_4Si$ as an internal standard.

TABLE 17

| Ex | NMR |
|---|---|
| 58 | 1.22–1.78(3H, m), 1.86–2.01(1H, m), 2.22(3H, s), 2.26–2.42(2H, m), 2.64–2.74(2H, m), 3.02–3.28(2H, m), 3.88(1H, d, J = 12.2 Hz), 4.42(1H, d, J = 12.2 Hz), 4.70–4.93(1H, br), 6.32(1H, d, J = 2.4 Hz), 6.65(1H, s), 6.85–6.98(1H, m), 7.00–7.12(2H, m), 7.18(1H, t, J = 7.8 Hz), 7.22–7.29(1H, m), 7.35–7.50(2H, m), 7.54–7.62(1H, m), 7.81(1H, s), 8.37(1H, s). |
| 62 | 1.12–1.32(4H, m), 1.56–1.72(2H, m), 1.83–1.96(2H, m), 2.22(3H, s), 2.36–2.45(1H, br), 2.54–2.79(1H, br), 3.04–3.23(1H, br), 3.29–3.38(1H, m), 3.44–3.57(1H, br), 4.52(1H, d, J = 4.9 Hz), 4.68–4.94(1H, br), 6.33(1H, d, J = 2.5 Hz), 6.36(1H, s), 6.93–7.09(2H, m), 7.16(1H, dt, J = 1.2, 7.8 Hz), 7.25(1H, t, J = 7.8 Hz), 7.33(1H, d, J = 7.8 Hz), 7.57(1H, d, J = 7.8 Hz), 7.84(1H, s), 8.09–8.18(1H, br), 8.38(1H, d, J = 2.4 Hz). |
| 67 | 2.22(3H, s), 2.55–2.90(1H, br), 2.60(3H, s), 3.10–3.35(1H, br), 3.50–3.65(1H, br), 4.80–4.95(1H, br), 6.34(1H, d, J = 2.4 Hz), 6.65(1H, s), 7.00–7.96(10H, m), 8.20(1H, s), 8.38(1H, d, J = 2.6 Hz), 10.57(1H, s). |
| 71 | 2.22(3H, s), 2.41–2.47(1H, br), 2.60–2.78(1H, br), 3.12–3.28(1H, br), 4.69–4.98(1H, br), 6.63(1H, d, J = 2.4 Hz), 6.63(1H, s), 7.02(1H, d, J = 7.8 Hz), 7.05–7.14(1H, br), 7.20(1H, dt, J = 1.5, 7.8 Hz), 7.28(1H, t, J = 7.8 Hz), 7.34–7.41(2H, m), 7.44(1H, t, J = 7.8 Hz), 7.61(2H, t, J = 7.8 Hz), 7.83–7.88(2H, m), 7.95(1H, s), 8.07(1H, s), 8.37(1H, d, J = 2.4 Hz), 10.47(1H, s). |
| 72 | 2.22(3H, s), 2.28–2.39(1H, br), 2.58–2.79(1H, br), 3.22–3.40(1H, br), 4.50–4.83(1H, br), 6.33(1H, d, J = 2.4 Hz), 6.65(1H, s), 7.03(1H, d, J = 7.8 Hz), 7.06–7.13(1H, br), 7.21(1H, dt, J = 1.5, 7.8 Hz), 7.24–7.33(2H, m), 7.37(1H, d, J = 7.8 Hz), 7.59(1H, d, J = 8.3 Hz), 7.71(2H, d, J = 8.8 Hz), 7.83–7.91(4H, m), 8.33(1H, d, J = 2.4 Hz), 10.56(1H, s). |
| 73 | 2.23(3H, s), 2.34–2.47(1H, br), 2.54–2.69(1H, br), 2.79(3H, d, J = 4.4 Hz), 3.00–3.28(1H, br), 4.71–4.90(1H, br), 6.34(1H, d, J = 2.4 Hz), 6.63(1H, s), 6.96–7.14(2H, m), 7.21(1H, t, J = 7.8 Hz), 7.29(1H, t, J = 7.8 Hz), 7.37(1H, d, J = 7.8 Hz), 7.45(1H, t, J = 7.8 Hz), 7.52–7.64(2H, m), 8.07(1H, s), 8.38(1H, d, J = 2.4 Hz), 8.41–8.49(1H, m), 10.50(1H, s). |
| 74 | 2.22(3H, s), 2.31(3H, s), 2.55–2.90(1H, br), 3.10–3.35(1H, br), 3.50–3.65(1H, br), 4.80–4.95(1H, br), 6.33(1H, d, J = 2.4 Hz), 6.60(1H, s), 6.90–7.61(10H, m), 7.84(1H, s), 8.38(1H, d, J = 2.4 Hz), 10.27(1H, s). |
| 76 | 2.22(3H, s), 2.60–2.90(1H, br), 3.05–3.35(1H, br), 3.50–3.65(1H, br), 4.51(2H, d, J = 5.1 Hz), 4.76–4.90(1H, br), 5.23(1H, t, J = 5.6 Hz), 6.33(1H, d, J = 2.4 Hz), 6.61(1H, s), 6.98–7.39(7H, m), 7.51–7.63(3H, m), 7.84(1H, s), 8.38(1H, d, J = 2.4 Hz), 10.33(1H, s). |
| 77 | 2.22(3H, s), 2.60–2.95(1H, br), 3.00–3.30(1H, br), 3.50–3.65(1H, br), 4.47(2H, d, J = 5.5 Hz), 4.75–4.95(1H, br), 5.13(1H, t, J = 5.6 Hz), 6.33(1H, d, J = 2.4 Hz), 6.61(1H, s), 6.99–7.39(7H, m), 7.56–7.61(3H, m), 7.84(1H, s), 8.37(1H, d, J = 2.4 Hz), 10.32(1H, s). |
| 78 | 2.22(3H, s), 2.72(2H, t, J = 7.0 Hz), 2.55–2.90(1H, br), 3.10–3.35(1H, br), 3.50–3.65(1H, br), 3.58–3.66(2H, m), 4.66(1H, t, J = 5.2 Hz), 4.80–4.95(1H, br), 6.33(1H, d, J = 2.4 Hz), 6.60(1H, s), 6.95–7.61(10H, m), 7.84(1H, s), 8.38(1H, d, J = 2.4 Hz), 10.29(1H, s). |
| 79 | 1.33(3H, d, J = 6.4 Hz), 2.22(3H, s), 2.55–2.90(1H, br), 3.05–3.30(1H, br), 3.50–3.65(1H, br), 4.67–4.76(1H, m), 4.75–4.90(1H, br), 5.20(1H, d, J = 4.0 Hz), 6.33(1H, d, J = 2.4 Hz), 6.60(1H, s), 7.00–7.39(7H, m), 7.52–7.61(3H, m), 7.84(1H, s), 8.38(1H, d, J = 2.4 Hz), 10.33(1H, s). |
| 81 | 2.22(3H, s), 2.45–2.55(1H, br), 2.70–2.80(1H, br), 3.15–3.25(1H, br), 3.42(2H, t, J = 6.1 Hz), 4.51(1H, q, J = 5.4 Hz), 4.69(1H, t, J = 5.9 Hz), 4.75–4.95(1H, br), 5.18(1H, d, J = 3.9 Hz), 6.34(1H, d, J = 2.4 Hz), 6.61(1H, s), 7.01(1H, d, J = 7.8 Hz), 7.03–7.15(1H, br), 7.20(1H, dt, J = 1.5, 7.8 Hz), |

TABLE 17-continued

| Ex | NMR |
|---|---|
|  | 7.25–7.35(3H, m), 7.38(1H, dd, J = 7.8, 1.5 Hz), 7.55–7.61(3H, m), 7.85(1H, s), 8.38(1H, d, J = 2.4 Hz), 10.3(1H, s). |
| 82 | 2.22(3H, s), 2.55–2.90(1H, br), 3.10–3.35(1H, br), 3.32(3H, s), 3.50–3.65(1H, br), 4.42(2H, s), 4.80–4.95(1H, br), 6.34(1H, d, J = 2.4 Hz), 6.61(1H, s), 7.00–7.39(7H, m), 7.55–7.64(3H, m), 7.85(1H, s), 8.38(1H, d, J = 2.4 Hz), 10.37(1H, s). |
| 83 | 2.22(3H, s), 2.42–2.48(1H, br), 2.66–2.93(1H, br), 3.09–3.27(1H, br), 3.38(2H, s), 4.69–5.00(1H, br), 6.33(1H, d, J = 2.4 Hz), 6.51(1H, s), 6.91(1H, s), 7.02(2H, d, J = 7.8 Hz), 7.04–7.15(1H, br), 7.20(1H, t, J = 7.8 Hz), 7.24–7.33(2H, m), 7.37(1H, d, J = 7.8 Hz), 7.46–7.63(4H, m), 7.84(1H, s), 8.38(1H, d, J = 2.4 Hz), 10.35(1H, s). |
| 84 | 2.22(3H, s), 2.37(2H, t, J = 7.8 Hz), 2.43–2.48(1H, br), 2.63–2.74(1H, br), 2.80(2H, t, J = 7.8 Hz), 3.19–3.24(1H, br), 4.75–4.94(1H, br), 6.34(1H, d, J = 2.4 Hz), 6.60(1H, s), 6.77(1H, s), 6.97(1H, d, J = 7.8 Hz), 7.03(1H, d, J = 7.8 Hz), 7.06–7.14(1H, br), 7.17–7.34(5H, m), 7.37(1H, dd, J = 1.0, 7.8 Hz), 7.44–7.52(1H, m), 7.59(1H, d, J = 7.8 Hz), 7.84(1H, d), 8.37(1H, d, J = 2.4 Hz), 10.31(1H, s). |
| 85 | 2.22(3H, s), 2.42–2.48(1H, br), 2.69–2.82(1H, br), 3.22–3.29(1H, br), 4.74–5.02(1H, br), 6.34(1H, d, J = 2.4 Hz), 6.62–6.67(2H, m), 7.03(1H, d, J = 7.8 Hz), 7.05–7.16(2H, m), 7.22(1H, dt, J = 1.4, 7.8 Hz), 7.27–7.33(2H, m), 7.36–7.44(3H, m), 7.51–7.65(3H, m), 7.84(1H, s), 7.99(1H, s), 8.38(1H, d, J = 2.4 Hz), 10.43(1H, s). |
| 86 | 2.22(3H, s), 2.55–2.90(1H, br), 3.10–3.35(1H, br), 3.50–3.65(1H, br), 4.80–4.95(1H, br), 6.33(1H, d, J = 2.4 Hz), 6.64(1H, s), 6.91–7.66(10H, m), 7.84(1H, s), 8.38(1H, d, J = 2.4 Hz), 10.57(1H, s). |
| 87 | 2.22(3H, s), 2.55–2.90(1H, br), 3.10–3.35(1H, br), 3.24(3H, s), 3.50–3.65(1H, br), 4.80–4.95(1H, br), 6.34(1H, d, J = 2.4 Hz), 6.66(1H, s), 7.00–7.40(5H, m), 7.57–7.69(3H, m), 7.84(1H, s), 7.95–8.00(1H, m), 8.26(1H, br), 8.38(1H, d, J = 2.4 Hz), 10.75(1H, s). |
| 88 | 2.05(3H, s), 2.22(3H, s), 2.32–2.47(1H, br), 2.55–2.78(1H, br), 2.99–3.28(1H, br), 4.70–4.98(1H, br), 6.33(1H, d, J = 2.4 Hz), 6.60(1H, s), 7.02(1H, d, J = 7.8 Hz), 7.04–7.15(1H, br), 7.17–7.39(6H, m), 7.60(1H, d, J = 8.3 Hz), 7.84(1H, s), 7.98(1H, s), 8.38(1H, d, J = 2.4 Hz), 9.99(1H, s), 10.37(1H, s). |
| 90 | 1.77–1.91(1H, m), 2.22(3H, s), 2.32–2.47(2H, m), 2.69–2.83(1H, br), 3.19–3.27(3H, m), 4.32–4.50(1H, m), 4.75–4.92(1H, br), 6.33(1H, d, J = 2.4 Hz), 6.42(1H, s), 6.91–7.07(2H, m), 7.17(1H, d, J = 1.5, 7.8 Hz), 7.24(1H, t, J = 7.8 Hz), 7.32(1H, dd, J = 1.5, 7.8 Hz), 7.59(1H, d, J = 8.3 Hz), 7.84(1H, s), 7.91(1H, s), 8.37(1H, d, J = 2.4 Hz), 8.65–8.76(1H, m). |
| 91 | 2.22(3H, s), 2.32–2.47(1H, br), 2.62–2.90(1H, br), 3.09–3.23(1H, br), 3.25–3.31(2H, m), 4.22–4.30(1H, br), 4.37–4.44(1H, m), 4.61–5.00(2H, m), 6.33(1H, d, J = 2.4 Hz), 6.45(1H, s), 6.93–7.07(2H, m), 7.18(1H, dt, J = 1.4, 7.8 Hz), 7.25(1H, t, J = 7.8 Hz), 7.31(1H, d, J = 7.8 Hz), 7.58(1H, d, J = 7.8 Hz), 7.83(1H, s), 8.37(1H, d, J = 2.4 Hz), 8.74–8.98(1H, br). |
| 92 | 1.04–1.12(1H, m), 2.07–2.19(2H, m), 2.22(3H, s), 2.34–2.45(1H, br), 2.57–2.93(1H, br), 3.02–3.27(1H, br), 3.33–3.51(1H, m), 4.62–4.97(2H, m), 6.33(1H, d, J = 2.4 Hz), 6.45(1H, s), 6.90–7.08(2H, m), 7.16(1H, t, J = 7.3 Hz), 7.24(1H, t, J = 7.3 Hz), 7.31(1H, d, J = 7.3 Hz), 7.59(1H, d, J = 7.3 Hz), 7.84(1H, s), 8.38(1H, s), 8.71–8.83(1H, br). |
| 105 | 2.22(3H, s), 2.55–2.90(1H, br), 3.05–3.30(1H, br), 3.50–3.65(1H, br), 4.45(2H, d, J = 5.9 Hz), 4.75–4.90(1H, br), 6.33(1H, d, J = 2.4 Hz), 6.47(1H, s), 6.95–7.58(9H, m), 7.82–7.95(4H, m), 8.37(1H, d, J = 2.6 Hz), 8.94(1H, s). |
| 109 | 2.22(3H, s), 2.41–2.47(1H, br), 2.55–2.64(1H, br), 3.09–3.26(1H, br), 4.46(2H, d, J = 4.9 Hz), 4.74–4.90(1H, br), 6.33(1H, d, J = 2.4 Hz), 6.49(1H, s), 6.95–7.10(2H, m), 7.17(1H, dt, J = 1.5, 7.8 Hz), 7.25(1H, dt, J = 1.5, 7.8 Hz), 7.29–7.36(3H, m), 7.48–7.60(3H., m), 7.77–7.84(3H, m), 8.37(1H, d, J = 2.4 Hz), 9.00(1H, s). |
| 110 | 2.22(3H, s), 2.40–2.50(1H, br), 2.67–2.89(1H, br), 3.11–3.23(1H, br), 4.73(2H, d, J = 5.4 Hz), 4.76–4.90(1H, br), 6.34(1H, d, J = 2.5 Hz), 6.41(1H, s), 6.99(1H, d, J = 7.8 Hz), 7.19(1H, t, J = 7.8 Hz), 7.26(1H, t, J = 7.8 Hz), 7.33(1H, d, J = 6.8 Hz), 7.61(1H, d, J = 8.3 Hz), 7.79–7.88(3H, m), 8.35–8.45(2H, m), 8.79(1H, d, J = 4.8 Hz), 9.30(1H, s). |
| 119 | 2.22(3H, s), 2.35–2.55(1H, br), 2.70(3H, s), 2.70–2.85(1H, br), 3.12–3.30(1H, br), 4.67(2H, brs), 4.75–4.90(1H, br), 6.34(1H, d, J = 2.5 Hz), 6.53(1H, s), 6.99(1H, d, J = 7.8 Hz), 7.00–7.12(1H, br), 7.19(1H, td, J = 7.8, 1.5 Hz), 7.26(1H, d, J = 7.8 Hz), 7.33(1H, d, J = 7.8 Hz), 7.55–7.70(3H, m), 7.84(1H, s), 8.23–8.33(1H, br), 8.39(1H, d, J = 2.5 Hz), 9.23(1H, brs). |
| 144 | 1.27(6H, s), 2.22(3H, s), 2.34–2.55(1H, br), 2.55–2.80(1H, br), 3.21–3.28(1H, br), 3.45(2H, s), 4.70–4.96(1H, br), 4.86(1H, t, J = 5.9 Hz), 6.32(1H, s), 6.33(1H, d, J = 2.5 Hz), 6.87–7.07(1H, br), 6.96(1H, d, J = 7.8 Hz), 7.15(1H, t, J = 7.3 Hz), 7.22(1H, t, J = 7.3 Hz), 7.33(1H, d, J = 7.3 Hz), 7.56(1H, d, J = 8.8 Hz), 7.74(1H, s), 7.83(1H, s), 8.37(1H, d, J = 3.5 Hz). |
| 162 | 2.24(3H, s), 2.34–2.45(1H, br), 2.57–2.70(1H, br), 3.06–3.20(1H, br), 4.69–4.99(1H, br), 6.36(1H, d, J = 2.5 Hz), 6.46(1H, s), 6.76(1H, d, J = 7.8 Hz), 7.02(1H, d, J = 8.3 Hz), 7.16(1H, dt, J = 1.5, 7.8 Hz), 7.24(1H, dt, J = 1.5, 7.8 Hz), 7.32(1H, dd, J = 1.5, 7.8 Hz), 7.36(1H, d, J = 7.8 Hz), 7.85(1H, dd, J = 1.5, 8.3 Hz), 7.91(1H, s), 8.09(1H, d, J = 1.5 Hz), 8.46(1H, d, J = 2.5 Hz). |
| 163 | 2.22(3H, s), 2.37–2.45(1H, br), 2.71–2.87(1H, br), 3.08–3.29(3H, m), 3.49(2H, t, J = 6.4 Hz), 4.70–4.92(1H, br), 6.36(1H, d, J = 2.5 Hz), 6.48(1H, s), 6.97(1H, d, J = 7.8 Hz), 7.03(1H, d, J = 8.8 Hz), 7.15(1H, dt, J = 1.5, 7.8 Hz), 7.25(1H, dt, J = 1.5, 7.8 Hz), 7.34(1H, dd, J = 1.8, 7.8 Hz), 7.84(1H, dd, J = 1.5, 8.8 Hz), 8.09(1H, d, J = 1.5 Hz), 8.47(1H, d, J = 2.5 Hz), 8.51(1H, t, J = 5.3 Hz). |
| 167 | 2.22(3H, s), 2.41(3H, s), 2.43–2.46(1H, br), 2.57–2.64(1H, br), 3.00–3.21(1H, br), 4.71–4.99(1H, br), 6.24–6.31(1H, br), 6.37(1H, s), 6.57–6.87(2H, m), 7.09(1H, t, J = 7.8 Hz), 7.15(1H, t, J = 7.8 Hz), 7.25–7.39(3H, m), 7.58(1H, s), 7.84(1H, s), 8.27(1H, s). |
| 169 | 1.04(6H, s), 1.70(2H, t, J = 6.3 Hz), 2.43–2.48(1H, br), 2.53–2.57(1H, br), 2.86–2.96(2H, br), 3.17–3.26(3H, m), 4.62–5.02(1H, br), 6.12–6.19(1H, m), 6.25(1H, s), 6.36–6.40(1H, br), 6.64–6.72(1H, br), 6.86–6.92(1H, br), 7.13–7.35(4H, m), 7.79(1H, s). |
| 171 | 1.94–2.09(1H, m), 2.26–2.45(2H, m), 2.53–2.73(1H, br), 3.04–3.19(3H, m), 3.28–3.51(2H, m), 3.57–3.68(1H, m), 4.57–5.04(1H, br), 6.21–6.30(2H, m), 6.47(1H, s), 6.65–6.75(1H, m), 6.84–6.91(1H, m), 7.12–7.37(9H, m), 7.76–7.83(1H, m). |
| 172 | 0.86(3H, t, J = 7.3 Hz), 0.97(3H, s), 1.33–1.44(2H, m), 1.60–1.77(2H, m), 2.33–2.47(1H, br), 2.54–2.71(1H, br), 2.85–2.98(2H, m), 3.16–3.26(3H, m), 4.72–5.03(1H, br), 6.13–6.20(1H, m), 6.25(1H, s), 6.33–6.42(1H, br), 6.60–6.72(1H, br), 6.81–6.92(1H, br), 7.12–7.29(3H, m), 7.33(1H, s), 7.75–7.84(1H, br). |

TABLE 17-continued

| Ex | NMR |
|---|---|
| 176 | 1.03(3H, d, J = 6.3 Hz), 1.48–1.60(1H, m), 1.99–2.10(1H, m), 2.24–2.47(2H, m), 2.54–2.80(2H, m), 3.10–3.38(4H, m), 4.72–4.93(1H, br), 6.35(1H, s), 6.38–6.43(1H, m), 6.61(1H, s), 6.64–6.75(2H, m), 7.14(1H, t, J = 7.8 Hz), 7.23(1H, t, J = 7.8 Hz), 7.29(1H, d, J = 7.8 Hz), 7.35(1H, s), 7.85(1H, s). |
| 180 | 2.06(3H, s), 2.32–2.44(1H, br), 2.61–2.79(1H, br), 2.98–3.20(1H, br), 4.78–4.99(1H, br), 6.45(1H, s), 6.70(1H, d, J = 7.8 Hz), 7.03(1H, d, J = 8.3 Hz), 7.16(1H, dt, J = 1.5, 7.8 Hz), 7.25(1H, dt, J = 1.5, 7.8 Hz), 7.32(1H, dd, J = 1.5, 7.8 Hz), 7.37(1H, s), 7.60(1H, s), 7.84(1H, dd, J = 1.5, 8.3 Hz), 7.92(1H, s), 8.09(1H, d, J = 1.5 Hz), 8.36(1H, s). |
| 188 | 1.07(6H, s), 1.71(2H, t, J = 6.4 Hz), 2.36–2.47(1H, br), 2.55–2.68(1H, br), 2.88–2.96(2H, br), 3.02–3.16(1H, br), 3.17–3.28(2H, br), 4.63–4.82(3H, m), 6.13–6.25(1H, m), 6.33–6.42(1H, br), 6.47(1H, s), 6.67–6.77(1H, m), 6.83–6.94(1H, m), 7.13–7.38(3H, m), 7.79–7.80(2H, m), 8.41(1H, t, J = 7.8 Hz), 8.79(1H, d, J = 4.9 Hz), 9.20–9.29(1H, m). |
| 213 | 1.04(6H, s), 1.69(2H, t, J = 6.8 Hz), 2.42–2.48(1H, br), 2.53–2.70(1H, br), 2.87–2.95(2H, br), 3.18–3.25(5H, m), 3.43–3.50(2H, m), 4.71(1H, t, J = 5.4 Hz), 4.73–4.86(1H, br), 6.10–6.19(1H, m), 6.27(1H, s), 6.34–6.40(1H, br), 6.61–6.71(1H, br), 6.80–6.92(1H, br), 7.12–7.32(3H, m), 8.31–8.40(1H, br). |
| 215 | 1.03(3H, d, J = 6.8 Hz), 1.47–1.60(1H, m), 2.00–2.10(1H, m), 2.25–2.47(2H, m), 2.57–2.82(2H, m), 3.14–3.50(8H, m), 4.73(1H, t, J = 5.4 Hz), 4.76–4.92(1H, br), 6.34–6.44(2H, m), 6.62(1H, s), 6.66–6.72(2H, m), 7.16(1H, t, J = 7.8 Hz), 7.22(1H, t, J = 7.8 Hz), 7.32(1H, d, J = 7.8 Hz), 8.43(1H, s). |
| 216 | 1.03(3H, d, J = 6.8 Hz), 1.50–1.60(1H, m), 2.00–2.05(1H, m), 2.25–2.40(2H, m), 2.41–2.55(1H, m), 2.70–2.80(1H, m), 3.20–3.40(7H, m), 3.47(2H, q, J = 5.9 Hz), 4.75–4.90(1H, br), 6.37(1H, s), 6.37–6.42(1H, m), 6.62(1H, s), 6.63–6.75(2H, m), 7.16(1H, t, J = 7.3 Hz), 7.23(1H, t, J = 7.3 Hz), 7.32(1H, d, J = 7.3 Hz), 8.42(1H, s). |
| 220 | 1.81–1.96(4H, m), 2.32–2.41(1H, br), 2.54–2.67(1H, br), 3.06–3.17(4H, m), 3.27–3.49(1H, br), 3.78(2H, s), 4.62–5.01(1H, br), 6.13–6.22(1H, m), 6.34(1H, s), 6.37–6.45(1H, m), 6.62–6.73(1H, m), 6.82–6.91(1H, m), 7.10–7.35(5H, m), 5.50–8.64(11H, br). |
| 221 | 1.02(3H, d, J = 5.9 Hz), 1.45–1.55(1H, m), 1.95–2.10(1H, m), 2.25–2.50(3H, m), 2.65–2.75(2H, m), 3.00–3.35(3H, m), 3.70–3.80(2H, m), 4.70–4.95(1H, m), 6.15–6.20(1H, m), 6.34(1H, s), 6.39(1H, s), 6.60–6.70(1H, br), 6.80–6.90(1H, br), 7.10–7.40(5H, m), 8.50–8.60(1H, br). |
| 222 | 1.02(3H, d, J = 5.9 Hz), 1.45–1.55(1H, m), 1.97–2.08(1H, m), 2.25–2.60(3H, m), 2.65–2.75(2H, m), 3.05–3.35(3H, m), 3.70–3.80(2H, m), 4.65–4.80(1H, br), 6.10–6.20(1H, m), 6.34(1H, s), 6.39(1H, s), 6.60–6.70(1H, br), 6.80–6.90(1H, br), 7.10–7.40(5H, m), 8.50–8.60(1H, br). |
| 223 | 1.04(6H, s), 1.69(2H, t, J = 6.4 Hz), 2.44–2.47(1H, br), 2.53–2.69(1H, br), 2.87–2.95(2H, br), 3.17–3.27(3H, m), 3.71–3.77(2H, m), 4.77–4.98(1H, br), 6.11–6.19(1H, m), 6.34(1H, s), 6.35–6.41(1H, br), 6.62–6.73(1H, br), 6.83–6.92(1H, br), 7.10–7.36(5H, m), 8.58(1H, s). |
| 224 | 1.95–2.09(1H, m), 2.27–2.36(1H, m), 2.42–2.48(1H, m), 2.52–2.58(1H, br), 3.11–3.20(1H, m), 3.23–3.33(2H, m), 3.35–3.51(2H, m), 3.58–3.66(1H, m), 3.74(2H, d, J = 3.9 Hz), 4.48–5.11(1H, br), 6.21–6.26(1H, m), 6.34(1H, s), 6.44–6.52(1H, br), 6.65–6.76(1H, br), 6.83–6.92(1H, m), 7.12(1H, s), 7.16–7.34(9H, m), 8.54–8.63(1H, br). |
| 225 | 0.86(3H, t, J = 7.3 Hz), 0.97(3H, s), 1.34–1.44(2H, m), 1.61–1.76(2H, m), 2.42–2.48(1H, br), 2.52–2.57(1H, br), 2.85–2.97(2H, m), 3.15–3.27(3H, m), 3.74(2H, d, J = 4.4 Hz), 4.70–5.03(1H, br), 6.11–6.20(1H, m), 6.34(1H, s), 6.36–6.45(1H, br), 6.62–6.74(1H, br), 6.82–6.95(1H, m), 7.10–7.34(5H, m), 8.53–8.64(1H, br). |
| 227 | 1.03(3H, d, J = 5.8 Hz), 1.48–1.60(1H, m), 1.99–2.10(1H, m), 2.24–2.36(2H, m), 2.70–2.81(1H, m), 3.00–3.42(5H, m), 3.69–3.80(2H, br), 4.78–4.82(1H, br), 6.39(1H, d, J = 7.8 Hz), 6.43(1H, s), 6.62(1H, s), 6.65–6.74(2H, m), 7.10–7.29(4H, m), 7.35(1H, d, J = 8.4 Hz), 8.65(1H, s). |
| 228 | 1.03(3H, d, J = 6.3 Hz), 1.50–1.60(1H, m), 1.95–2.10(1H, m), 2.20–2.40(2H, m), 2.70–2.80(1H, m), 3.00–3.40(5H, m), 3.70–3.80(2H, m), 4.70–4.95(1H, br), 6.39(1H, d, J = 7.8 Hz), 6.43(1H, s), 6.62(1H, s), 6.65–6.75(2H, m), 7.10–7.30(4H, m), 7.35(1H, d, J = 8.4 Hz), 8.64(1H, s). |
| 230 | 0.90(6H, d, J = 5.9 Hz), 2.23–2.50(4H, m), 2.55–2.75(1H, br), 2.80–3.00(2H, br), 3.01–3.20(1H, br), 3.25–3.40(1H, m), 3.70–3.80(2H, m), 4.75–4.90(1H, br), 6.30–6.40(1H, m), 6.43(1H, s), 6.60(1H, s), 6.68(1H, d, J = 8.3 Hz), 6.72(1H, d, J = 6.8 Hz), 7.10–7.30(4H, m), 7.35(1H, d, J = 7.4 Hz), 8.63(1H, s). |
| 238 | 2.23(3H, s), 2.33–2.46(1H, br), 2.54–2.79(1H, br), 2.98–3.27(1H, br), 4.62–4.97(1H, br), 6.24(1H, s), 6.37(1H, d, J = 2.4 Hz), 7.07–7.54(6H, m), 7.75–7.92(2H, m), 8.05(1H, s). |
| 243 | 1.20–1.85(6H, m), 2.22(3H, s), 2.25–2.90(5H, m), 3.00–4.35(5H, m), 4.45–4.70(1H, m), 4.75–4.90(1H, br), 6.33(1H, d, J = 2.5 Hz), 6.39(1H, s), 6.98(1H, d, J = 7.8 Hz), 7.00–7.12(1H, br), 7.16(1H, t, J = 7.1 Hz), 7.25(1H, t, J = 7.3 Hz), 7.37(1H, d, J = 7.4 Hz), 7.57(1H, d, J = 7.8 Hz), 7.83(1H, s), 8.38(1H, d, J = 2.4 Hz), 8.40–8.55(1H, m). |
| 244 | 1.20–1.75(6H, m), 2.22(3H, s), 2.30–2.50(2H, m), 2.65–3.01(3H, m), 3.20–3.40(3H, m), 3.70–3.80(1H, m), 4.07(1H, s), 4.54(0.5H, t, J = 5.4 Hz), 4.63(0.5H, t, J = 5.4 Hz), 4.65–4.80(1H, br), 6.33(1H, d, J = 2.5 Hz), 6.40(1H, s), 6.98(1H, d, J = 7.8 Hz), 7.00–7.10(1H, br), 7.17(1H, dt, J = 1.5, 7.8 Hz), 7.25(1H, dt, J = 1.0, 7.8 Hz), 7.37(1H, d, J = 7.3 Hz), 7.57(1H, d, J = 7.8 Hz), 7.83(1H, s), 8.38(1H, d, J = 2.5 Hz), 8.47–8.60(1H, br). |

The structures of the compounds of the present invention are shown in Table 18. These compounds can be easily synthesized by methods that are self-evident to an ordinarily skilled person, or with modified methods. The 'No' in the Table indicates compound number.

TABLE 18

| No | R¹ | R² | R³ | R⁴ | R⁵ |
|---|---|---|---|---|---|
| A1 | —NH-(4-HO₂C—Ph) | Cl | 3-Me-pra | H | H |
| A2 | —NH-(2-HO₂C—Ph) | Cl | 3-Me-pra | H | H |
| A3 | —NH-(4-Me₂N—Ph) | Cl | 3-Me-pra | H | H |
| A4 | —NH-(4-cyano-Ph) | Cl | 3-Me-pra | H | H |
| A5 | —NH-(3-F₃C—Ph) | Cl | 3-Me-pra | H | H |
| A6 | —NH-(2-MeO—Ph) | Cl | 3-Me-pra | H | H |
| A7 | —NH-(2-F—Ph) | Cl | 3-Me-pra | H | H |
| A8 | —NHCH2-(2-H₂NOC—Ph) | Cl | 3-Me-pra | H | H |
| A9 | —NH-(6-HO-3-py) | Cl | 3-Me-pra | H | H |
| A10 | —NH-(6-Cl-pyridazin-3-yl) | Cl | 3-Me-pra | H | H |
| A11 | —NH-(6-Me-2-py) | Cl | 3-Me-pra | H | H |
| A12 | —NH-(5-H₂NOC-2-py) | Cl | 3-Me-pra | H | H |
| A13 | —NH-(2-thia) | Cl | 3-Me-pra | H | H |
| A14 | —NH-(1-Me-2-imid) | Cl | 3-Me-pra | H | H |
| A15 | —NH-(pyrazin-2-yl) | Cl | 3-Me-pra | H | H |
| A16 | —N(Me)-(6-HO-3-py) | Cl | 3-Me-pra | H | H |
| A17 | —NHCH₂-(4-H₂NOC-2-py) | Cl | 3-Me-pra | H | H |
| A18 | —N(Me)CH₂-(3-py) | Cl | 3-Me-pra | H | H |
| A19 | —NHCH₂-(4-F-2-py) | Cl | 3-Me-pra | H | H |
| A20 | —NHCH₂-(pyrimidin-2-yl) | Cl | 3-Me-pra | H | H |
| A21 | 2-H₂NOC-pyrr | Cl | 3-Me-pra | H | H |
| A22 | 2-H₂NOC-pipe | Cl | 3-Me-pra | H | H |
| A23 | [structure: —NH—C(=O)—CH₂—NH—CH₂-(2-pyridyl)] | Cl | 3-Me-pra- | H | H |
| A24 | [structure: —NH—C(=O)—CH₂—NH—CH₂-(6-OH-2-pyridyl)] | Cl | 3-Me-pra- | H | H |
| A25 | [structure: —NH—C(=O)—CH₂—NH—CH₂-(6-CONH₂-2-pyridyl)] | Cl | 3-Me-pra- | H | H |

TABLE 18-continued
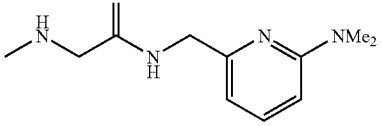
| No | R¹ | R² | R³ | R⁴ | R⁵ |
|---|---|---|---|---|---|
| A26 | 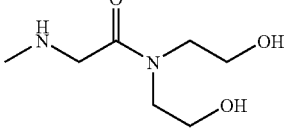 | Cl | 3-Me-pra- | H | H |
| A27 | 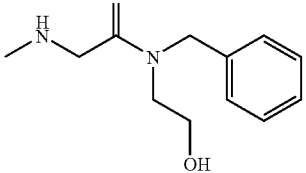 | Cl | 3-Me-pra- | H | H |
| A28 | 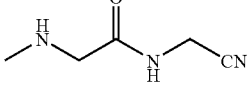 | Cl | 3-Me-pra- | H | H |
| A29 | 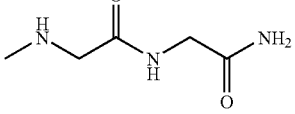 | Cl | 3-Me-pra- | H | H |
| A30 | 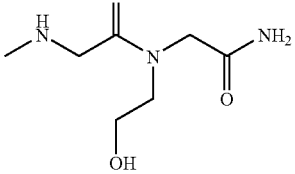 | Cl | 3-Me-pra- | H | H |
| A31 | | Cl | 3-Me-pra- | H | H |
| A32 | 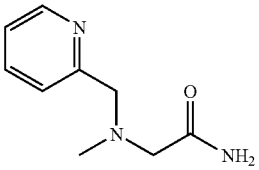 | Cl | 3-Me-pra- | H | H |

TABLE 18-continued

| No | R¹ | R² | R³ | R⁴ | R⁵ |
|---|---|---|---|---|---|
| A33 | (pyridin-4-yl-CH₂-N(Me)-CH₂-C(O)NH₂) | Cl | 3-Me-pra- | H | H |
| A34 | (6-hydroxypyridin-2-yl-CH₂-N(Me)-CH₂-C(O)NH₂) | Cl | 3-Me-pra- | H | H |
| A35 | (6-chloropyridin-2-yl-CH₂-N(Me)-CH₂-C(O)NH₂) | Cl | 3-Me-pra- | H | H |
| A36 | (6-methylpyridin-2-yl-CH₂-N(Me)-CH₂-C(O)NH₂) | Cl | 3-Me-pra- | H | H |
| A37 | (HOCH₂CH₂-N(Me)-CH₂-(6-methylpyridin-2-yl)) | Cl | 3-Me-pra- | H | H |
| A38 | (HOCH₂CH₂-N(Me)-CH₂-(6-chloropyridin-2-yl)) | Cl | 3-Me-pra- | H | H |

TABLE 18-continued

| No | R¹ | R² | R³ | R⁴ | R⁵ |
|---|---|---|---|---|---|
| A39 | (2-hydroxyethyl)(methyl)amino-CH₂-(6-HO-2-py) | Cl | 3-Me-pra- | H | H |
| A40 | (2-hydroxyethyl)(methyl)amino-CH₂-(4-py) | Cl | 3-Me-pra- | H | H |
| A41 | (2-hydroxy-2-methylethyl)(methyl)amino-CH₂-(6-HO-2-py) | Cl | 3-Me-pra- | H | H |
| A42 | (2-hydroxyethyl)(methyl)amino-CH₂-(2-pyrimidinyl) | Cl | 3-Me-pra- | H | H |
| A43 | N-methyl-N,N-bis((2-pyridyl)methyl)amino | Cl | 3-Me-pra- | H | H |
| A44 | —NHCH₂-(2-py) | Br | 3-Me-pra- | H | H |
| A45 | —NH(CH₂)₂OH | Br | 3-Me-pra- | H | H |
| A46 | —NHCH₂CONH₂ | Br | 3-Me-pra- | H | H |
| A47 | —NH₂ | Br | 3-Me-pra- | H | H |
| A48 | —NHCH₂-(2-py) | Me | 3-Me-pra- | H | H |
| A49 | —NH(CH₂)₂OH | Me | 3-Me-pra- | H | H |
| A50 | —NHCH₂CONH₂ | Me | 3-Me-pra- | H | H |
| A51 | —NH₂ | Me | 3-Me-pra- | H | H |
| A52 | —NH(CH₂)₂OH | Me | pyrr- | H | H |
| A53 | —NHCH₂-(6-HO-2-py) | Me | pyrr- | H | H |
| A54 | —NHCH₂-(2-py) | Me | pyrr- | H | H |
| A55 | —N((CH₂)₂OH)₂ | Me | pyrr- | H | H |
| A56 | —NH₂ | Me | pyrr- | H | H |
| A57 | —NHCH₂CONH₂ | Me | 3-Me-pyrr- | H | H |
| A58 | —NHCH₂-(2-py) | Me | 3-Me-pyrr- | H | H |
| A59 | —NH₂ | Me | 3-Me-pyrr- | H | H |
| A60 | —NH(CH₂)₂OH | Me | 3-Me-pyrr- | H | H |
| A61 | —NHCH₂CONH₂ | Me | 3,3-diF-pyrr- | H | H |

TABLE 18-continued

| No | R¹ | R² | R³ | R⁴ | R⁵ |
|---|---|---|---|---|---|
| A62 | —NHCH₂CONH₂ | Me | 3,4-diMe-pyrr- | H | H |
| A63 | —NH₂ | Me | 3,3-diF-pyrr- | H | H |
| A64 | —NH₂ | Me | 3,4-diMe-pyrr- | H | H |
| A65 | —NHCH₂-(6-HO-2-py) | CF₃ | 3-Me-pra- | H | H |
| A66 | —NHCH₂-(6-Me-2-py) | CF₃ | 3-Me-pra- | H | H |
| A67 | —NH—CH₂-(benzimidazol-2-yl) | CF₃ | 3-Me-pra- | H | H |
| A68 | —NHCH₂-(6-HO-2-py) | CF₃ | 3-Me-pra- | H | H |
| A69 | —N((CH₂)₂OH)₂ | CF₃ | 3-Me-pra- | H | H |
| A70 | —NHCH₂-(6-HO-2-py) | CF₃ | pyrr- | H | H |
| A71 | —NHCH₂-(2-py) | CF₃ | pyrr- | H | H |
| A72 | —N((CH₂)₂OH)₂ | CF₃ | pyrr- | H | H |
| A73 | —N((CH₂)₂OH)₂ | Cl | 3-Me-pyrr- | H | H |
| A74 | —NHCH₂-(2-py) | Cl | 2-H₂NOC-pyrr- | H | H |
| A75 | —NHCH₂-(2-py) | Cl | 3-HO-pipe- | H | H |
| A76 | —NHCH₂-(2-py) | CF₃ | 3-HO-pipe- | H | H |
| A77 | —NHCH₂-(2-py) | Cl | 3-MeO-pyrr- | H | H |
| A78 | —NHCH₂-(2-py) | CF₃ | 3-MeO-pyrr- | H | H |
| A79 | —NHCH₂-(2-py) | Cl | 4-NC-pipe- | H | H |
| A80 | —NHCH₂-(2-py) | Cl | 3,4-diMe-pyrr- | H | H |
| A81 | —NH(CH₂)₂OH | Cl | 2,4-diMe-pyrr- | H | H |
| A82 | —NHCH₂-(2-py) | Cl | 1,2-diMe-pyrrol-1-yl | H | H |
| A83 | —NH(CH₂)₂OH | Cl | 2-methylisoindolin-2-yl | H | H |
| A84 | —NHCH₂CONH₂ | Cl | 1-methyl-1,2,4-triazol-1-yl | H | H |
| A85 | —NH(CH₂)₂OH | CF₃ | 1-methyltetrazol-1-yl | H | H |
| A86 | —NHCH₂-(2-py) | CF₃ | 1,2,5-triMe-pyrrol-1-yl | H | H |

TABLE 18-continued

| No | R¹ | R² | R³ | R⁴ | R⁵ |
|---|---|---|---|---|---|
| A87 | —NHCH₂-(2-py) | Cl | 3-Me-pra- | H | 7-Me |
| A88 | —NHCH₂-(2-py) | Cl | 3-Me-pyrr- | H | 7-Me |
| A89 | —NHCH₂-(2-py) | Cl | 3-Me-pra- | H | 7-Cl |
| A90 | —NHCH₂-(2-py) | Cl | 3-Me-pyrr- | H | 7-Cl |
| A91 | —NHCH₂-(2-py) | CF₃ | 3-Me-pra | H | 7-Me |
| A92 | —NHCH₂-(2-py) | CF₃ | 3-Me-pyrr | H | 7-Me |
| A93 | —NHCH₂-(2-py) | CF₃ | 3-Me-pra | H | 7-Cl |
| A94 | —NHCH₂-(2-py) | CF₃ | 3-Me-pyrr | H | 7-Cl |
| A95 | —NHCH₂-(2-py) | Cl | 3-Me-pra | H | 8-Me |
| A96 | —NHCH₂-(2-py) | Cl | 3-Me-pyrr | H | 8-Me |
| A97 | —NHCH₂-(2-py) | Cl | 3-Me-pra | H | 8-Cl |
| A98 | —NHCH₂-(2-py) | Cl | 3-Me-pyrr | H | 8-Cl |
| A99 | —NHCH₂-(2-py) | CF₃ | 3-Me-pra | H | 8-Me |
| A100 | —NHCH₂-(2-py) | CF₃ | 3-Me-pyrr | H | 8-Me |
| A101 | —NHCH₂-(2-py) | CF₃ | 3-Me-pra | H | 8-Cl |
| A102 | —NHCH₂-(2-py) | CF₃ | 3-Me-pyrr | H | 8-Cl |
| A103 | —NHCH₂-(2-py) | Cl | H | 3-Me-pra- | H |
| A104 | —NHCH₂-(2-py) | Cl | H | 3-Me-pyrr- | H |
| A105 | —NHCH₂CONH₂ | Cl | H | 3-Me-pyrr- | H |
| A106 | —NHCH₂-(2-py) | Cl | H | pyrr- | H |
| A107 | —NHCH₂-(2-py) | CF₃ | H | 3-Me-pra- | H |
| A108 | —NHCH₂-(2-py) | CF₃ | H | 3-Me-pyrr- | H |
| A109 | —NHCH₂CONH₂ | CF₃ | H | 3-Me-pyrr- | H |
| A110 | —NHCH₂-(2-py) | CF₃ | H | pyrr- | H |
| A111 | —NH(CH₂)₂OH | Cl | 3,3-diF-pyrr | H | H |
| A112 | —NHCH₂CONH₂ | Cl | 3,3-diF-pyrr | H | H |
| A113 | —NH(CH₂)₂OH | CF₃ | 3,3-diF-pyrr | H | H |
| A114 | —NHCH₂CONH₂ | CF₃ | 3,3-diF-pyrr | H | H |
| A115 | —NH(CH₂)₂OH | Cl | 3-CF₃-pyrr | H | H |
| A116 | —NHCH₂CONH₂ | Cl | 3-CF₃-pyrr | H | H |
| A117 | —NH(CH₂)₂OH | CF₃ | 3-CF₃-pyrr | H | H |
| A118 | —NHCH₂CONH₂ | CF₃ | 3-CF₃-pyrr | H | H |
| A119 | —NH(CH₂)₂OH | Cl | 2,5-dihydropyrrol-1-yl | H | H |
| A120 | —NHCH₂CONH₂ | Cl | 2,5-dihydropyrrol-1-yl | H | H |
| A121 | —NH₂ | Cl | 2,5-dihydropyrrol-1-yl | H | H |
| A122 | —NH(CH₂)₂OH | Cl | 3,4-diMe-1-pyrr | H | H |
| A123 | —NHCH₂CONH₂ | Cl | 3,4-diMe-1-pyrr | H | H |
| A124 | —NH₂ | Cl | 3,4-diMe-1-pyrr | H | H |
| A125 | —NHCH₂CONH₂ | Cl | Me-[3-methyl-2,5-dihydropyrrol-1-yl] | H | H |
| A126 | —NH₂ | Cl | Me-[3-methyl-2,5-dihydropyrrol-1-yl] | H | H |
| A127 | —NHCH₂CONH₂ | Cl | 3,4-diHO-1-pyrr | H | H |
| A128 | —NH₂ | Cl | 3,4-diHO-1-pyrr | H | H |
| A129 | —NH-(3-HOCH₂—(E)—CH=CH—Ph) | CF₃ | 3-Me-pra | H | H |
| A130 | —NH-(3-HO₂C—(E)—CH=CH—Ph) | CF₃ | 3-Me-pra | H | H |
| A131 | —NH-(3-Ph—(E)—CH=CH—Ph) | CF₃ | 3-Me-pra | H | H |
| A132 | —NH-2-(5-H₂NOC—(E)—CH=CH—Py) | CF₃ | 3-Me-pra | H | H |
| A133 | OMe | CF₃ | H₂N—(Ac)N— | H | H |
| A134 | OEt | CF₃ | H₂N—(Ac)N— | H | H |
| A135 | OEt | CF₃ | H₂N—(Boc)N— | H | H |
| A136 | OiPr | CF₃ | H₂N—(Boc)N— | H | H |

TABLE 18-continued

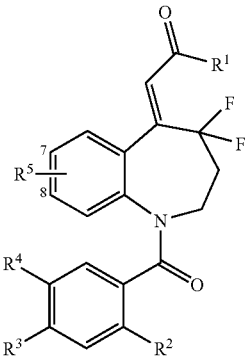

| No | R¹ | R² | R³ | R⁴ | R⁵ |
|---|---|---|---|---|---|
| A137 | OEt | Cl | H₂N—(Boc)N— | H | H |
| A138 | OiPr | Cl | H₂N—(Boc)N— | H | H |
| A139 | OEt | CF₃ | H₂N—HN— | H | H |
| A140 | OiPr | CF₃ | H₂N—HN— | H | H |
| A141 | OEt | Cl | H₂N—HN— | H | H |
| A142 | OiPr | Cl | H₂N—HN— | H | H |
| A143 | —NHCH₂CONH₂ | CF₃ | 3-Me-pra | Me | H |
| A144 | —NH₂ | CF₃ | 3-Me-pra | Me | H |
| A145 | —NHCH₂CONH₂ | CF₃ | 3-Me-pra | F | H |
| A146 | —NH₂ | CF₃ | 3-Me-pra | F | H |
| A147 | —NHCH₂CONH₂ | CF₃ | 3-Me-pyrr | F | H |
| A148 | —NH₂ | CF₃ | 3-Me-pyrr | F | H |
| A149 | —NH₂ | CF₃ | 3-Me-pyrr | Me | H |
| A150 | —NH-(4-H₂NOC—Ph) | CF₃ | 3-Me-pra | H | H |
| A151 | —NH-(3-H₂NOC—Ph) | CF₃ | 3-Me-pra | H | H |
| A152 | —NH-(3-Me—Ph) | CF₃ | 3-Me-pra | H | H |
| A153 | —NH-(4-HOCH₂—Ph) | CF₃ | 3-Me-pra | H | H |
| A154 | —NH-(3-HOCH₂—Ph) | CF₃ | 3-Me-pra | H | H |
| A155 | —NH-(4-MeOCH₂—Ph) | CF₃ | 3-Me-pra | H | H |
| A156 | —NHCH₂-(4-H₂NOC—Ph) | CF₃ | 3-Me-pra | H | H |
| A157 | —NH-(3-Ms—Ph) | CF₃ | 3-Me-pra | H | H |
| A158 | —NH-(3-Ac—Ph) | CF₃ | 3-Me-pra | H | H |
| A159 | —NHCH₂-(4-H₂NO₂S—Ph) | CF₃ | 3-Me-pra | H | H |
| A160 | —NH-(2-HO-cHex) | CF₃ | 3-Me-pra | H | H |
| A161 | —NH-(3-H₂NOCCH₂—Ph) | CF₃ | 3-Me-pra | H | H |
| A162 | —NH-(3-H₂NOC(CH₂)₂—Ph) | CF₃ | 3-Me-pra | H | H |
| A163 | —NH-(3-H₂NOC—(E)—CH=CH—Ph) | CF₃ | 3-Me-pra | H | H |
| A164 | —NH-(3-AcNH—Ph) | CF₃ | 3-Me-pra | H | H |
| A165 | —NH-(4-H₂NOC—Ph) | CF₃ | 3-Me-pyrr | H | H |
| A166 | —NH-(3-H₂NOC—Ph) | CF₃ | 3-Me-pyrr | H | H |
| A167 | —NH-(3-Me—Ph) | CF₃ | 3-Me-pyrr | H | H |
| A168 | —NH-(4-HOCH₂—Ph) | CF₃ | 3-Me-pyrr | H | H |
| A169 | —NH-(3-HOCH₂—Ph) | CF₃ | 3-Me-pyrr | H | H |
| A170 | —NH-(4-MeOCH₂—Ph) | CF₃ | 3-Me-pyrr | H | H |
| A171 | —NH-(3-Ms—Ph) | CF₃ | 3-Me-pyrr | H | H |
| A172 | —NH-(3-Ac—Ph) | CF₃ | 3-Me-pyrr | H | H |
| A173 | —NHCH₂-(4-H₂NO₂S—Ph) | CF₃ | 3-Me-pyrr | H | H |
| A174 | —NH-(2-HO-cHex) | CF₃ | 3-Me-pyrr | H | H |
| A175 | —NH-(3-H₂NOCCH₂—Ph) | CF₃ | 3-Me-pyrr | H | H |
| A176 | —NH-(3-H₂NOC(CH₂)₂—Ph) | CF₃ | 3-Me-pyrr | H | H |
| A177 | —NH-(3-H₂NOC—(E)—CH=CH—Ph) | CF₃ | 3-Me-pyrr | H | H |
| A178 | —NH-(3-AcNH—Ph) | CF₃ | 3-Me-pyrr | H | H |
| A179 | —NH(4-H₂NOC—Ph) | Cl | 3-Me-pyrr | H | H |
| A180 | —NH-(3-H₂NOC—Ph) | Cl | 3-Me-pyrr | H | H |
| A181 | —NH-(3-Me—Ph) | Cl | 3-Me-pyrr | H | H |
| A182 | —NH-(4-HOCH₂—Ph) | Cl | 3-Me-pyrr | H | H |
| A183 | —NH-(3-HOCH₂—Ph) | Cl | 3-Me-pyrr | H | H |
| A184 | —NH-(4-MeOCH₂—Ph) | Cl | 3-Me-pyrr | H | H |
| A185 | —NH-(3-Ms—Ph) | Cl | 3-Me-pyrr | H | H |
| A186 | —NH-(3-Ac—Ph) | Cl | 3-Me-pyrr | H | H |
| A187 | —NHCH₂-(4-H₂NO₂S—Ph) | Cl | 3-Me-pyrr | H | H |
| A188 | —NH-(2-HO-cHex) | Cl | 3-Me-pyrr | H | H |
| A189 | —NH-(3-H₂NOCCH₂—Ph) | Cl | 3-Me-pyrr | H | H |
| A190 | —NH-(3-H₂NOC(CH₂)₂—Ph) | Cl | 3-Me-pyrr | H | H |
| A191 | —NH-(3-H₂NOC—(E)—CH=CH—Ph) | Cl | 3-Me-pyrr | H | H |
| A192 | —NH-(3-AcNH—Ph) | Cl | 3-Me-pyrr | H | H |

The invention claimed is:

1. A 4,4-difluoro-1,2,3,4-tetrahydro-5H-1-benzazepine compound represented by Formula (I) or a pharmaceutically acceptable salt thereof:

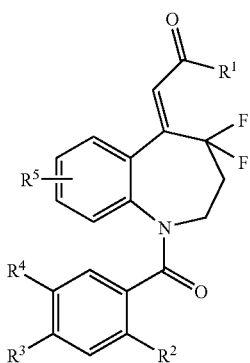

(I)

wherein the symbols have the following meanings:

$R^1$: —OH, —O-lower alkyl, or an optionally substituted amino;

$R^2$: lower alkyl which may be substituted with one or more halogen, or halogen;

$R^3$ and $R^4$: one is —H, lower alkyl, or halogen, and the other is an optionally substituted nonaromatic cyclic amino or an optionally substituted aromatic cyclic amino; and $R^5$: —H, lower alkyl, or halogen.

2. The compound or pharmaceutically acceptable salt thereof according to claim 1, wherein $R^1$ is —OH, —O-lower alkyl, a group represented by the following Formula (II), or a group represented by the following Formula (III):

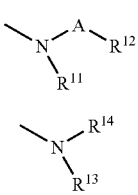

(II)

(III)

wherein the symbols have the following meanings:

A: a single bond, lower alkylene, or -lower alkylene-C(=O)—;

$R^{11}$: lower alkyl which may be substituted with a group selected from the group consisting of —OH, —O-lower alkyl, —CO$_2$H, —CO$_2$-lower alkyl, and carbamoyl which may be substituted with one or two lower alkyl, or —H;

$R^{12}$: (1) when A is a single bond or lower alkylene, $R^{12}$ is aryl, cycloalkyl, aromatic heterocycle, or nonaromatic heterocycle, each of which may be substituted, or —H, —OH, —O-lower alkyl, —CO$_2$H, —CO$_2$-lower alkyl, or carbamoyl which may be substituted with one or two lower alkyls; and (2) when A is -lower alkylene-C(=O)—, $R^{12}$ is a group represented by the above Formula (III), or a group represented by the following Formula (IV),

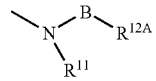

(IV)

B: a single bond, or lower alkylene;

$R^{12A}$: aryl, cycloalkyl, aromatic heterocycle, or nonaromatic heterocycle, each of which may be substituted, or —H, —OH, —O-lower alkyl, —CO$_2$H, —CO$_2$-lower alkyl, or carbamoyl which may be substituted with one or two lower alkyls; and $R^{13}$ and $R^{14}$: optionally substituted nonaromatic cyclic amino, bonded together with an adjacent nitrogen atom.

3. The compound or pharmaceutically acceptable salt thereof according to claim 2, wherein $R^1$ is a group represented by Formula (II), or a group represented by Formula (III).

4. The compound or pharmaceutically acceptable salt thereof according to claim 3, wherein $R^3$ is an optionally substituted nonaromatic cyclic amino, or an optionally substituted aromatic cyclic amino; $R^4$ is —H, lower alkyl, or halogen; and $R^5$ is —H.

5. The compound or pharmaceutically acceptable salt thereof according to claim 4, wherein $R^4$ is —H.

6. The compound according to any one of claim 1 to claim 5, wherein the compound is selected from the group consisting of.

(2Z)-2-{1-[2-chloro-4-(3-methyl-1H-pyrazol-1-yl)benzoyl]-4,4-difluoro-1,2,3,4-tetrahydro-5H-1-benzazepin-5-ylidene}-N-(pyridin-2-ylmethyl)acetamide;

(2Z)-N-(2-amino-2-oxoethyl)-2-[1(2-chloro-4-pyrrolidin-1-ylbenzoyl)-4,4-difluoro-1,2,3,4-tetrahydro-5H-1-benzazepin-5-ylidene]acetamide;

(2Z)-2-{4,4-difluoro-1-[4-(3-methyl-1H-pyrazol-1-yl)-2-(trifluoromethyl)benzoyl]-1,2,3,4-tetrahydro-5H-1-benzazepin-5-ylidene}acetamide;

(2Z)-N-(2-amino-2-oxoethyl)-2-{4,4-difluoro-1-[4-[(3R)-3-methylpyrrolidin-1-yl]-2-(trifluoromethyl)benzoyl]-1,2,3,4-tetrahydro-5H-1-benzazepin-5-ylidene}acetamide;

(2Z)-2-{4,4-difluoro-1-[4-[(3R)-3-methylpyrrolidin-1-yl]-2-(trifluoromethyl)benzoyl]-1,2,3,4-tetrahydro-5H-1-benzazepin-5-ylidene}-N-(2-hydroxyethyl)acetamide;

(2Z)-N-(2-amino-2-oxoethyl)-2-{4,4-difluoro-1-[4-(3S)-3-methylpyrrolidin-1-yl]-2-(trifluoromethyl)benzoyl]-1,2,3,4-tetrahydro-5H-1-benzazepin-5-ylidene}acetamide;

(2Z)-2-{4,4-difluoro-1-[4[(3-methyl-1H-pyrazol-1-yl)-2-(trifluoromethyl)benzoyl]-1,2,3,4-tetrahydro-5H-1-benzazepin-5-ylidene]-N-(2-hydroxyethyl)acetamide;

(2Z)-N-(2-amino-2-oxoethyl)-2-(1{2-chloro-4-[(3R)-3-methylpyrrolidin-1-yl]benzoyl}-4,4-difluoro-1,2,3,4-tetrahydro-5H-1-benzazepin-5-ylidene)acetamide;

(2Z)-N-(2-amino-2-oxoethyl)-2-(1-{2-chloro-4-[(3S)-3-methylpyrrolidin-1-yl]benzoyl}-4,4-difluoro-1,2,3,4-tetrahydro-5H-1-benzazepin-5-ylidene)acetamide;

(2Z)-2-{4,4-difluoro-1-[4-(4-methyl-1H-pyrazol-1-yl)-2-(trifluoromethyl)benzoyl]-1,2,3,4-tetrahydro-5H-1-benzazepin-5-ylidene}acetamide;

(2Z)-N-(2-amino-2-oxoethyl)-2-{1-[4-(3,4-dimethylpyrrolidin-1yl)-2-(trifluoromethyl)benzoyl]-4,4-difluoro-1,2,3,4-tetrahydro-5H-1-benzazepin-5-ylidene}acetamide;

(2Z)-2-{4,4-difluoro-1-[2-methyl-4-(3-methyl-1H-pyrazol-1-yl)benzoyl]1,2,3,4-tetrahydro-5H-1-benzazepin-5-ylidene}acetamide; and a pharmaceutically acceptable salt thereof.

7. A pharmaceutical composition comprising the compound or pharmaceutically acceptable salt thereof of claim 1 as an active ingredient.

8. A 4,4-difluoro-1,2,3,4-tetrahydro-5H-1-benzazepine compound represented by Formula (V) or a pharmaceutically acceptable salt thereof

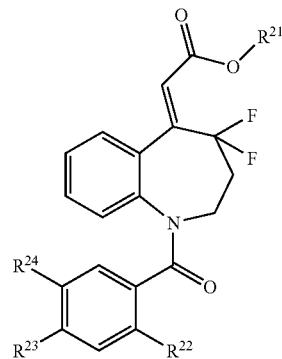

(V)

wherein the symbols have the following meanings:

$R^{21}$: lower alkyl;

$R^{22}$: chloro or trifluoromethyl; and $R^{23}$ and $R^{24}$: one is —H, and the other is an optionally protected hydrazino group.

* * * * *

UNITED STATES PATENT AND TRADEMARK OFFICE
CERTIFICATE OF CORRECTION

PATENT NO. : 7,169,772 B2 Page 1 of 1
APPLICATION NO. : 10/495494
DATED : January 30, 2007
INVENTOR(S) : Koshio et al.

It is certified that error appears in the above-identified patent and that said Letters Patent is hereby corrected as shown below:

Claim 6, COL. 62, Line 37, change "of." to -- of: --.

Signed and Sealed this

First Day of May, 2007

JON W. DUDAS
*Director of the United States Patent and Trademark Office*